United States Patent
Couch et al.

(10) Patent No.: US 10,962,478 B2
(45) Date of Patent: Mar. 30, 2021

(54) SPECTRAL IMAGING APPARATUS AND METHODS

(71) Applicant: AXON DX, LLC, Earlysville, VA (US)

(72) Inventors: Philip R. Couch, Honiton (GB); Kent A. Murphy, Arlington, VA (US)

(73) Assignee: AXON DX, LLC, Earlysville, VA (US)

( * ) Notice: Subject to any disclaimer, the term of this patent is extended or adjusted under 35 U.S.C. 154(b) by 9 days.

(21) Appl. No.: 16/496,614

(22) PCT Filed: Mar. 20, 2018

(86) PCT No.: PCT/US2018/023253
§ 371 (c)(1),
(2) Date: Sep. 23, 2019

(87) PCT Pub. No.: WO2018/175377
PCT Pub. Date: Sep. 27, 2018

(65) Prior Publication Data
US 2020/0018702 A1    Jan. 16, 2020

Related U.S. Application Data

(60) Provisional application No. 62/475,921, filed on Mar. 24, 2017.

(51) Int. Cl.
*G01N 21/64* (2006.01)
*G01N 33/483* (2006.01)
(Continued)

(52) U.S. Cl.
CPC .......... *G01N 21/6428* (2013.01); *G01J 3/027* (2013.01); *G01J 3/2803* (2013.01);
(Continued)

(58) Field of Classification Search
CPC .......... G01N 21/6428; G01N 33/4833; G01N 2201/103; G01N 2201/12; G01N 21/6489;
(Continued)

(56) References Cited

U.S. PATENT DOCUMENTS 6,403,947 B1    6/2002   Hoyt et al.
6,495,818 B1 *  12/2002  Mao .................... G01C 11/025
                                              250/226

(Continued)

FOREIGN PATENT DOCUMENTS

WO      00/75636       12/2000
WO      2015/095603    6/2015
(Continued)

OTHER PUBLICATIONS

International Search Report for PCT/US2018/023253, dated May 31, 2018, 3 pages.
(Continued)

*Primary Examiner* — Dominic J Bologna
(74) *Attorney, Agent, or Firm* — Nixon & Vanderhye P.C.

(57) ABSTRACT

An imaging system images a sample across one or more wavelengths. A light source illuminates a sample with one or more wavelengths of light, and an image sensor detects light from the illuminated sample. A linear variable long pass filter is positioned to filter light reflected from the sample to pass to the image sensor multiple different wavelength bands having different cut-off wavelengths. Wavelengths of light on one side of the cut-off wavelength are blocked and wavelengths of light on the other side of the cut-off wavelength are passed as multiple different long pass wavelength bands for detection by the image sensor. The image sensor detects light for each of the multiple different long pass wavelength bands from the sample. Data processing cir-
(Continued)

cuitry converts the detected light for the multiple different long pass wavelength bands for the sample into corresponding different long pass wavelength band data sets for the sample.

20 Claims, 14 Drawing Sheets

(51) Int. Cl.
   G02B 21/00   (2006.01)
   G02B 21/26   (2006.01)
   G01J 3/28    (2006.01)
   G01J 3/44    (2006.01)
   G02B 21/36   (2006.01)
   G01N 21/33   (2006.01)
   G02B 21/16   (2006.01)
   G01N 21/01   (2006.01)
   G01N 21/17   (2006.01)
   G01J 3/02    (2006.01)
   G01J 3/12    (2006.01)

(52) U.S. Cl.
   CPC ........... *G01J 3/2823* (2013.01); *G01J 3/4406* (2013.01); *G01N 21/01* (2013.01); *G01N 21/17* (2013.01); *G01N 21/33* (2013.01); *G01N 21/64* (2013.01); *G01N 21/6458* (2013.01); *G01N 21/6489* (2013.01); *G01N 33/4833* (2013.01); *G02B 21/008* (2013.01); *G02B 21/0036* (2013.01); *G02B 21/0064* (2013.01); *G02B 21/0076* (2013.01); *G02B 21/16* (2013.01); *G02B 21/26* (2013.01); *G02B 21/36* (2013.01); *G01J 2003/1234* (2013.01); *G01J 2003/2806* (2013.01); *G01N 2021/6421* (2013.01); *G01N 2201/103* (2013.01); *G01N 2201/12* (2013.01)

(58) Field of Classification Search
   CPC ....... G01N 2021/6421; G01N 21/6458; G01N 21/01; G01N 21/17; G01N 21/33; G01N 21/64; G02B 21/0036; G02B 21/0064; G02B 21/0076; G02B 21/008; G02B 21/26; G02B 21/36; G02B 21/16; G01J 2003/1234; G01J 3/027; G01J 3/2803; G01J 3/4406; G01J 2003/2806; G01J 3/2823
   See application file for complete search history.

(56) References Cited

U.S. PATENT DOCUMENTS

| | | | |
|---|---|---|---|
| 7,420,679 B2 | 9/2008 | Treado et al. | |
| 7,573,575 B2 | 8/2009 | Shakespeare et al. | |
| 7,858,953 B2 | 12/2010 | Hughes et al. | |
| 8,014,569 B2 | 9/2011 | Durkin et al. | |
| 8,244,021 B2 | 8/2012 | Lett et al. | |
| 8,285,024 B2 | 10/2012 | Lett et al. | |
| 8,686,363 B1 | 4/2014 | Timlin et al. | |
| 9,304,039 B2 | 4/2016 | Tack et al. | |
| 9,429,743 B2 | 8/2016 | Garsha et al. | |
| 2002/0001080 A1 | 1/2002 | Miller et al. | |
| 2003/0215791 A1 | 11/2003 | Garini et al. | |
| 2008/0272312 A1 | 11/2008 | Tuschel | |
| 2014/0061486 A1 | 3/2014 | Bao et al. | |
| 2014/0295415 A1 | 10/2014 | Rolland et al. | |
| 2014/0310635 A1 | 10/2014 | Lett et al. | |
| 2016/0131583 A1* | 5/2016 | Bamford | G01N 21/6428 435/29 |
| 2016/0314583 A1* | 10/2016 | Couch | H04N 5/2256 |

FOREIGN PATENT DOCUMENTS

| | | |
|---|---|---|
| WO | 2016/049544 | 3/2016 |
| WO | 2016/111308 | 7/2016 |
| WO | 2017/079212 | 5/2017 |

OTHER PUBLICATIONS

Written Opinion of the IS for PCT/US2018/023253, dated May 31, 2018, 13 pages.
International Preliminary Report on Patentability for PCT/US2018/023253, dated Jun. 6, 2019, 31 pages.
Semrock, "Flatness of Dichroic Beamsplitters Affects Focus and Image Quality" retrieved May 11, 2017 from htps://www.semrock.com/flatness-of-dichroic-beamsplitters-affects-focus-and-image-qual . . . 10 pages.
Ximea, "xiSpec—Hyperspectral Cameras with USB3 Vision" retrieved May 11, 2017 from https://www.ximea.com/usb3-vision-camera/hyperspectral-usb3-cameras-mini, 6 pages.
M. Jayapala et al., "Monolithic Integration of Flexible Spectral Filters with CMOS Image Sensors at Wafer Level for Low Cost Hyperspectral Imaging," *Proceedings of the 2013 International Image Sensor Workshop*, Jun. 2013, pp. 193-196.
A. Lambrechts et al., "A CMOS-Compatible Integrated Approach to Hyper- and Multispectral Imaging," *2014 IEEE International Electron Devices Meeting (IEDM)*, Dec. 15-17, 2014, 4 pages.
Y. Wan et al., "Compact Characterization of Liquid Absorption and Emission Spectra Using Linear Variable Filters Integrated with a CMOS Imaging Camera," *Scientific Reports*, Jul. 2016, pp. 1-9.
Cheng-Hao Ko et al., "Analytical Modeling of a Linear Variable Filter for Computational Hyperspectral Imaging," *Fourier Transform Spectroscopy and Hyperspectral Imaging and Sounding of the Environment OSA Technical Digest Online, Optical Society of America*, Mar. 2015, 1 page.
Schultz et al., "Hyperspectral Imaging: A Novel Approach for Microscopic Analysis," *Cytometry*, vol. 43, 2001, Mar. 15, 2001, pp. 239-247.
Huebschman et al., "Characteristics and Capabilities of the Hyperspectral Imaging Microscope," *IEEE Engineering in Medicine and Biology*, Jul./Aug. 2002, pp. 104-117.

* cited by examiner

SPECTRAL IMAGING APPARATUS AND METHODS

This application is the U.S. national phase of International Application No. PCT/US2018/023253 filed 20 Mar. 2018, which designated the U.S. and claims the priority and benefit of U.S. Provisional Patent Application 62/475,921, filed Mar. 24, 2017, the entire contents of each of which are hereby incorporated by reference.

Circulating tumor cells (CTCs) in the blood stream play a critical role in establishing metastases. CTCs and circulating stem cells (CSC) are non-limiting examples of rare circulating cells. The clinical value of CTCs as a biomarker for early cancer detection, diagnosis, prognosis, prediction, stratification, and pharmacodynamics have been widely explored in recent years. Methods, reagents, and devices for rapid detection of cancer cells as well as methods and apparatus for analysis, aggregation, and output of detected cancer cells or fragments are described in commonly-assigned PCT patent application number, PCT/US2014/071292, filed on Dec. 18, 2014, and PCT/US2016/060010, filed on Nov. 2, 2016, the contents of both of which are incorporated herein by reference.

A biomarker may be made using a stain containing an organic fluorophore conjugated to an affinity molecule which binds to protein, protein fragments, or other targets in the test sample. The stained sample is illuminated with light and the stain fluoresces. A camera attached to a microscope captures an image of the sample. The areas where the fluorophore/affinity molecule combination are bound to the target of interest (e.g., CTCs) appears as colored regions in the sample image, with the color being dictated by the fluorescence spectrum of the fluorophore applied to the sample. In addition to the visible spectrum, the fluorescence signal may be detected in the infra-red or ultra-violet regions, depending on emission spectrum of the particular fluorophore.

More recently, a class of synthetic fluorophores called quantum dot (QDOT) fluorophores is available as a stain material for biological staining and imaging applications. A quantum dot is a nano-crystalline luminescent semiconductor material. The use of quantum dots provides several advantages over traditional organic fluorophores for use in biological staining applications. Example advantages include narrow emission band peaks, broad absorption spectra, intense signals, and strong resistance to bleaching or other degradation.

QDOTs are stimulated with a common wavelength (usually in the UV spectrum), and different fluorophores (different size QDOTs) emit fluorescence at multiple different wavelengths, e.g., 6-20 wavelengths. Each fluorophore emits a distinct color or nominal wavelength. An image sensor is needed that can differentiate different wavelengths emitted by different fluorophores. A typical black and white camera sensor is divided into a large number of pixels, where each pixel may be an individual CMOS or CCD photodetector with an optical response covering and beyond the human visible range. In a typical color camera, the pixels are masked with color filters so that only one quarter of these pixels respond to red light, one quarter respond to blue light, and the rest respond to green light. So for each color (and especially red and blue), both the resolution and the light collecting power of the color camera (i.e., the camera's sensitivity) is significantly reduced compared to a black and white camera. In fluorescence image detection applications, both high resolution and high sensitivity to typically very weak fluorescence are desirable but can be difficult to achieve for a color camera. The technology described below provides both high resolution and high sensitivity for hyperspectral imaging over multiple wavelengths, e.g., color imaging, that is advantageous for fluorescence image detection applications specifically and for other multiple wavelength imaging applications generally.

SUMMARY

Example embodiments include an imaging system for imaging a sample that includes a light source to illuminate a sample with one or more wavelengths of light, an image sensor to detect light from the illuminated sample, and a linear variable long pass filter positioned to filter light reflected from the sample to pass to the image sensor multiple different wavelength bands having different cut-off wavelengths. Wavelengths of light on one side of the cut-off wavelength are blocked, and wavelengths of light on the other side of the cut-off wavelength are passed as multiple different long pass wavelength bands for detection by the image sensor. The image sensor detects light for each of the multiple different long pass wavelength bands from the sample. Data processing circuitry converts the detected light for the multiple different long pass wavelength bands for the sample into corresponding different long pass wavelength band data sets for the sample; selects a first one of the long pass wavelength band data sets having a first cut-off wavelength and a second different one of the long pass wavelength band data sets having a second different cut-off wavelength; negates the values of the second long pass wavelength band data set; combines the first long pass wavelength band data set and the negated second long pass wavelength band data set to generate a first pass band that selects image data from the sample with wavelengths between the first and second cut-off wavelengths; and processes the selected image data in the first pass band to identify marked objects in the sample.

The light source, in one example application, illuminates the sample with a fluorescence wavelength of light. In a further example application, the light is ultraviolet light to illuminate fluorophores present in the sample. Marked objects in the sample may be detected, e.g., quantum dot fluorophores, organic fluorophores, or autofluorescence, and one or more parameters associated with a detected marked object determined. Coordinate locations of detected marked cell objects in the sample may also be determined and used for further imaging and/or processing of images of the marked objects.

In example applications, an affinity molecule binds to objects present in the sample. The affinity molecule may be one of an antibody, bacteriophage, scaffold protein, aptamer, lectin, peptide, engineered polypeptide mimetic, or small molecule designed to target specific objects or specific components of objects for detection.

In an example application, the marked objects in the sample include (i) rare cells including circulating tumor cells, circulating stem cells, circulating fetal cells, circulating endothelial cells, circulating cancer associated fibroblasts, circulating cancer associated macrophages, (ii) organisms in a biome, or (iii) pathogen contaminants in biological samples or food and water supplies.

In example applications, autofluorescence of the objects could be used to detect biological and non-biological objects in food or water.

In example applications, autofluorescence of the objects could be used to detect objects during one or more chemical processes, oil processing, or one or more manufacturing processes.

In example applications, the sample is on or in a microscope slide, a microtiter plate, a filter, an enzyme-linked immunosorbent assay (ELISA) strip, a lateral flow strip, or a microarray.

The data processing circuitry, in one example application, is configured to select the first long pass wavelength band data set and the second long pass wavelength band data set based on one or more configurable parameters.

The data processing circuitry, in one example application, is configured to: select a third one of the long pass wavelength band data sets having a third cut-off wavelength and a fourth different one of the long pass wavelength band data sets having a fourth different cut-off wavelength; negate the values of the fourth long pass wavelength band data set; combine the third long pass wavelength band data set and the negated fourth long pass wavelength band data set to generate a second pass band that selects image data from the sample with wavelengths between the third and fourth cut-off wavelengths; and process the selected image data in the second pass band to identify marked objects in the sample. In addition, the data processing circuitry may be configured to select a fifth one of the long pass wavelength band data sets having a fifth cut-off wavelength and a sixth different one of the long pass wavelength band data sets having a sixth different cut-off wavelength; negate the values of the sixth long pass wavelength band data set; combine the fifth long pass wavelength band data set and the negated sixth long pass wavelength band data set to generate a third pass band that selects image data from the sample with wavelengths between the fifth and sixth cut-off wavelengths; and process the selected image data in the third pass band to identify marked objects in the sample.

The data processing circuitry, in one example application, may be further configured to select the first, second, third, fourth, fifth, and sixth long pass wavelength band data sets based on one or more configurable parameters.

In one example embodiment, the first, second, and third pass bands implement a linear variable band pass filter.

In another example embodiment, the linear variable long pass filter has a first set of size dimensions and is partitioned to create a linear variable long pass filter with a second set of size dimensions smaller than the first set of size dimensions. The second set of size dimensions more closely align with imaging capabilities of the image sensor.

In another example embodiment, the imaging system includes a scanning mechanism to allow the image sensor to detect light for each of the multiple different long pass wavelength bands from the sample. The scanning mechanism moves the sample relative to the image sensor. The data processing circuitry collects and stores in memory portions of image data of the sample for each wavelength band, and at the end of the scan of the sample, combine the stored portions of image data for each wavelength band to produce a hyperspectral image data set for the sample.

In an example application for this example embodiment, the sample is divided into multiple areas, and the scanning mechanism moves the sample relative to the image sensor both length-wise and width-wise to permit the data processing circuitry to collect and store in memory portions of image data of the sample for each wavelength band to generate a set of images in each of the wavelength bands for each of the multiple areas of the sample. For each area of the sample, the data processing circuitry processes the set of wavelength band images to generate a set of bandpass images and to combine the bandpass images to produce a hyperspectral image data set for all the areas of sample.

Example embodiments include an imaging system for imaging a sample that includes a light source to illuminate a sample with one or more wavelengths of light, an image sensor to detect light from the illuminated sample, and a linear variable long pass filter positioned to filter light reflected from the sample to pass to the image sensor multiple different wavelength bands having different cut-off wavelengths. Wavelengths of light on one side of the cut-off wavelength are blocked, and wavelengths of light on the other side of the cut-off wavelength are passed as multiple different short pass wavelength bands for detection by the image sensor. The image sensor detects light for each of the multiple different short pass wavelength bands from the sample. Data processing circuitry converts the detected light for the multiple different short pass wavelength bands for the sample into corresponding different short pass wavelength band data sets for the sample; selects a first one of the short pass wavelength band data sets having a first cut-off wavelength and a second different one of the short pass wavelength band data sets having a second different cut-off wavelength; negates the values of the second short pass wavelength band data set; combine the first short pass wavelength band data set and the negated second short pass wavelength band data set to generate a first pass band that selects image data from the sample with wavelengths between the first and second cut-off wavelengths; and processes the selected image data in the first pass band to identify marked objects in the sample.

In example applications, the data processing circuitry selects the first short pass wavelength band data set and the second pass wavelength band data set based on one or more configurable parameters. The first, second, and third pass bands may be used implement a linear variable band pass filter.

In example applications, the data processing circuitry selects a third one of the short pass wavelength band data sets having a third cut-off wavelength and a fourth different one of the short pass wavelength band data sets having a fourth different cut-off wavelength; negates the values of the fourth short pass wavelength band data set; combines the third short pass wavelength band data set and the negated fourth short pass wavelength band data set to generate a second pass band that selects image data from the sample with wavelengths between the third and fourth cut-off wavelengths; and processes the selected image data in the second pass band to identify marked objects in the sample. The data processing circuitry may further select a fifth one of the short pass wavelength band data sets having a fifth cut-off wavelength and a sixth different one of the short pass wavelength band data sets having a sixth different cut-off wavelength; negate the values of the sixth short pass wavelength band data set; combine the fifth short pass wavelength band data set and the negated sixth short pass wavelength band data set to generate a third pass band that selects image data from the sample with wavelengths between the fifth and sixth cut-off wavelengths; and process the selected image data in the third pass band to identify marked objects in the sample.

Example embodiments provide a method for imaging a sample. The steps include illuminating a sample with one or more wavelengths of light; detecting with an image sensor light from the illuminated sample; filtering with a linear variable long pass filter light reflected from the sample to pass to the image sensor multiple different wavelength bands having different cut-off wavelengths, where wavelengths of light on one side of the cut-off wavelength are blocked and wavelengths of light on the other side of the cut-off wavelength are passed as multiple different long pass wavelength bands for detection by the image sensor; the image sensor detecting light for each of the multiple different long pass wavelength bands from the sample; converting the detected light for the multiple different long pass wavelength bands for the sample into corresponding different long pass wavelength band data sets for the sample; selecting a first one of the long pass wavelength band data sets having a first cut-off wavelength and a second different one of the long pass wavelength band data sets having a second different cut-off wavelength; negating the values of the second long pass wavelength band data set; combining the first long pass wavelength band data set and the negated second long pass wavelength band data set to generate a first pass band that selects image data from the sample with wavelengths between the first and second cut-off wavelengths; and processing the selected image data in the first pass band to identify marked objects in the sample.

Example embodiments provide a further method for imaging a sample. The steps include illuminating a sample with one or more wavelengths of light; detecting with an image sensor light from the illuminated sample; filtering with a linear variable long pass filter light reflected from the sample to pass to the image sensor multiple different wavelength bands having different cut-off wavelengths, where wavelengths of light on one side of the cut-off wavelength are blocked and wavelengths of light on the other side of the cut-off wavelength are passed as multiple different long pass wavelength bands for detection by the image sensor; the image sensor detecting light for each of the multiple different long pass wavelength bands from the sample; converting the detected light for the multiple different short pass wavelength bands for the sample into corresponding different short pass wavelength band data sets for the sample; selecting a first one of the short pass wavelength band data sets having a first cut-off wavelength and a second different one of the short pass wavelength band data sets having a second different cut-off wavelength; negating the values of the second short pass wavelength band data set; combining the first short pass wavelength band data set and the negated second short pass wavelength band data set to generate a first pass band that selects image data from the sample with wavelengths between the first and second cut-off wavelengths; and processing the selected image data in the first pass band to identify marked objects in the sample.

The above aspects and example embodiments will be better understood and appreciated in conjunction with the following detailed description taken together with the accompanying figures.

DETAILED DESCRIPTION OF EXAMPLE EMBODIMENTS

To facilitate understanding of this disclosure set forth herein, a number of terms are defined below. Generally, the nomenclature used herein and the procedures in biology, biochemistry, organic chemistry, medicinal chemistry, pharmacology, optics, data processing, image processing, etc. described herein are generally well known and commonly employed in the art. Unless defined otherwise, all technical and scientific terms used herein generally have the same meaning as commonly understood in the art to which this disclosure belongs.

The term "sample" refers to any sample obtained from a subject, including, but not limited to, blood, plasma, broncheoalveolar lavage fluid, pleural fluid, fine needle aspirate, cervical smear, tissue, urine, stool, etc. Although a microscope slide is described as the substrate of choice for purposes of this discussion, any solid or porous substrate may be employed in accordance with the principles disclosed herein.

Fluorophores are examples of labels or signaling molecules that provide a detectable signal, either directly or through interaction with one or more additional members of a signal producing system. Fluorescent labels, where the wavelength of light absorbed by the fluorophore may generally range from about 300 to about 900 nm, usually from about 400 to about 800 nm, and the emission maximum may typically occur at a wavelength ranging from about 500 to about 800 nm.

Figure 1:
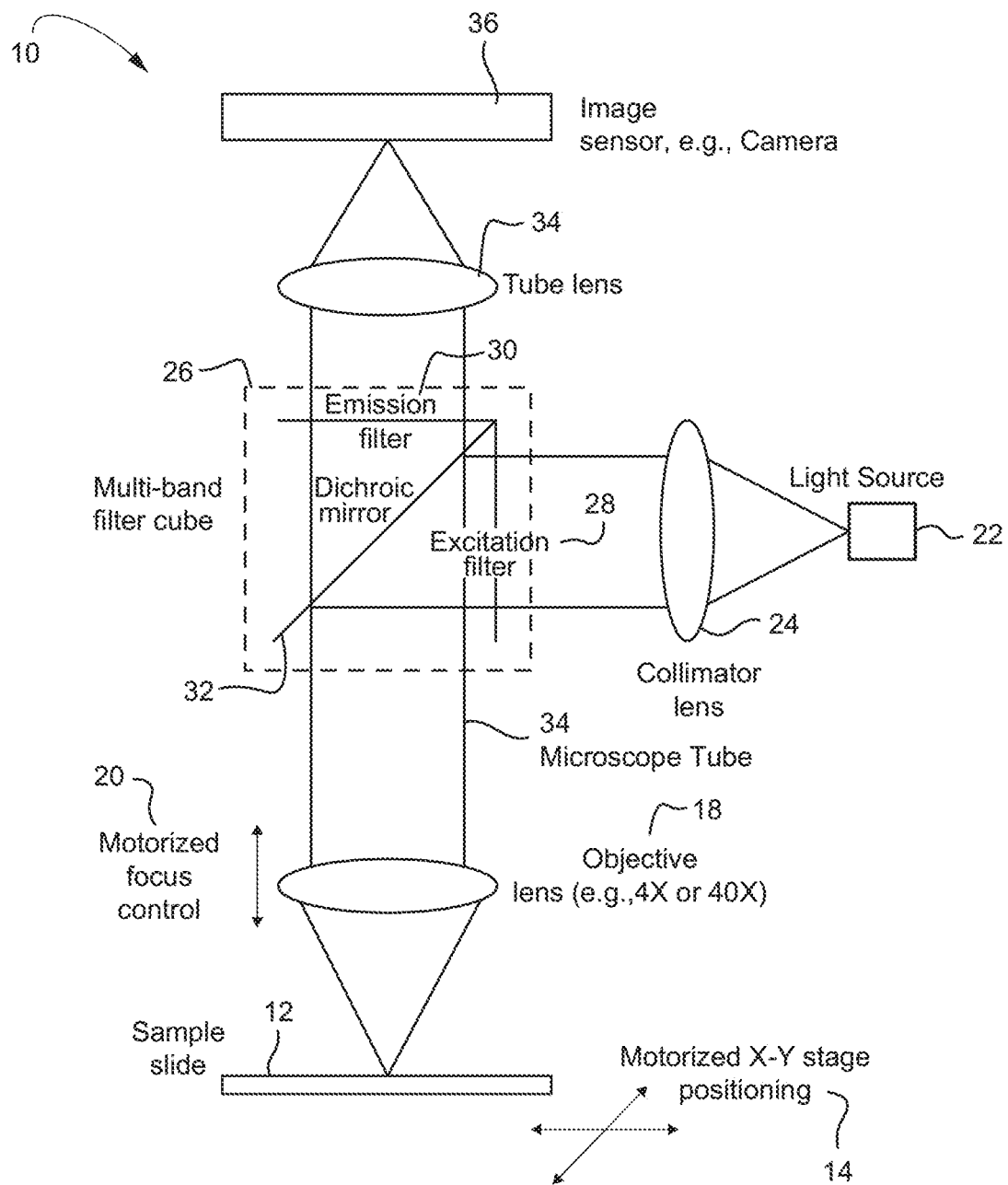
FIG. 1 depicts a non-limiting example of a fluorescence imaging system.

A non-limiting example embodiment of an optical instrument/optical fluorescence imaging system 10 is shown in FIG. 1. The sample to be searched for rare cells and/or rare cell fragments (both being encompassed by the term cell objects) is on a microscope slide 12 which may be moved in X and Y directions by a motorized stage 14. Above the stage 14 is one or more microscope objective lenses 18 coupled by a microscope tube 34, with motorized focus control 20, and elements of an epi-fluorescence microscope including a multi-band fluorescence filter 26 cube contained in the tube 34, tube lens 35, and an image sensor 36, e.g., a sensitive camera, etc.

The filter cube 26 includes a dichroic mirror 32 which passes the fluorescence emission wavelength(s) but reflects the excitation wavelengths. Emission wavelengths are further filtered by an emission filter 30 (described in detailed example embodiments below) before passing to the image sensor 36. A light source 22, such as one or more LED sources, is collimated at lens 24 and filtered by an excitation filter 28 before being reflected towards the sample by the dichroic mirror 32 in the filter cube 26. Different excitation wavelengths may be selected by enabling LEDs of different wavelengths in an example embodiment where conventional organic fluorophores are used.

The objective lens assembly 18 is motorized so that it may be focused by automated control 20, and objectives of different magnification may be selected, e.g., 4× and 40×.

Figure 2:
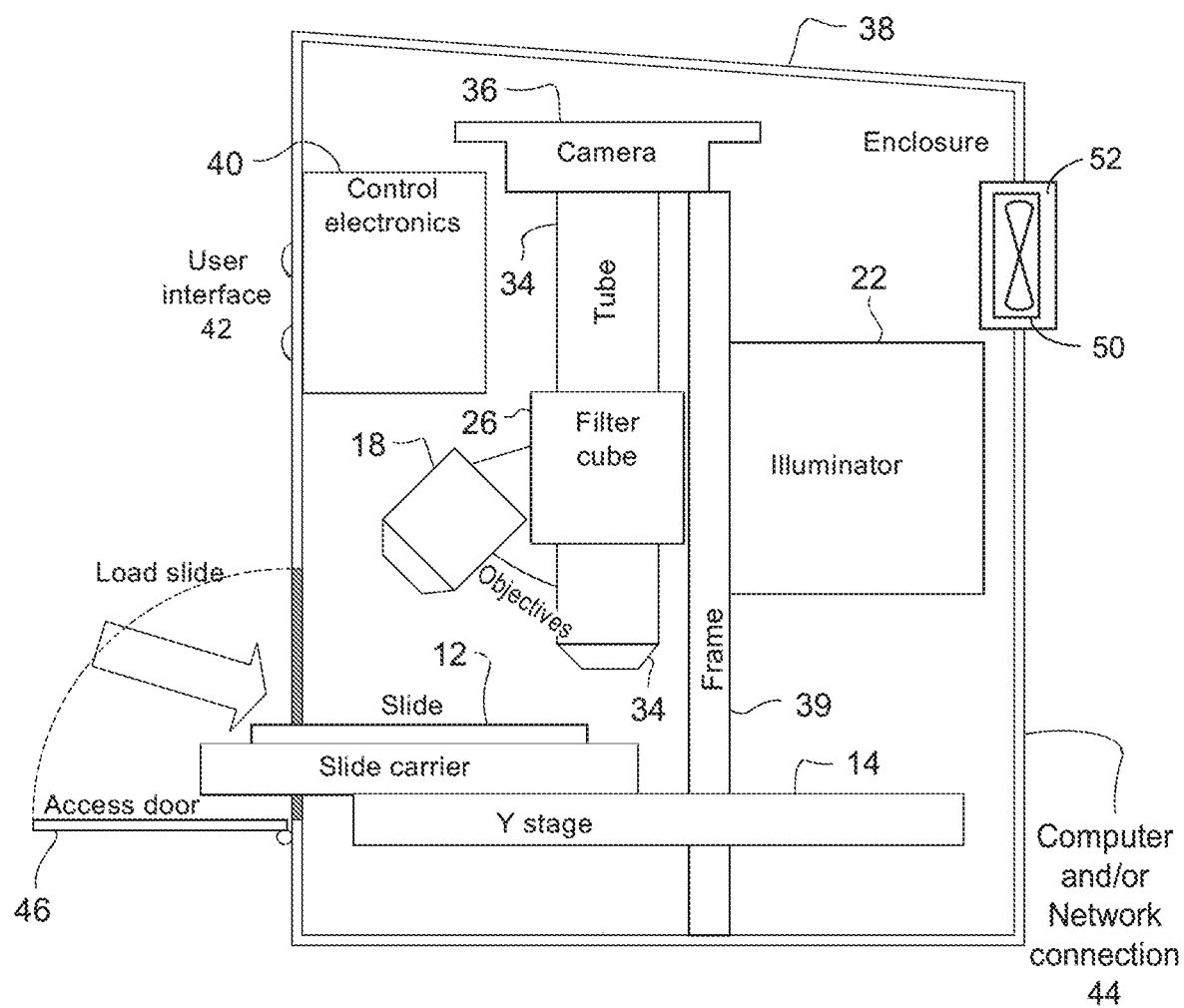
FIG. 2 depicts a non-limiting example implementation of the fluorescence imaging system from FIG. 1 in a housing with an access door.

FIG. 2 shows an example implementation of an optical/image fluorescence processing system provided in a housing 38 with an access door 46 and a frame 39 upon which various elements are mounted. The housing 38 excludes most ambient light and protects the user from intense illumination inside the box. Control electronics 40 are provided to drive motors, activate/deactivate the LEDs and the laser, etc. Optionally, some or all control may be accomplished by one or more computers attached via a data connection such as USB, Ethernet, WiFi, etc. This data connection may also be used to distribute information from the optical system via data communication network(s). Alternatively, all computer control hardware is included within the instrument so that it may operate stand-alone and at likely faster speeds.

Debris may be introduced inside the enclosure when the access door 46 is open. Accordingly, the optical/image processing system may be provided with a fan system 50 and/or a filtration system 52. The fan system 50 and/or a filtration system 52 may be provided in the housing 38 to circulate air into and/or out of the enclosure of the optical/image processing system. The filtration system 52 may include one or more air filters to filter out debris (e.g., dust) from entering the enclosure from outside of the optical/image processing system and to filter the air in the enclosure.

Figure 3:
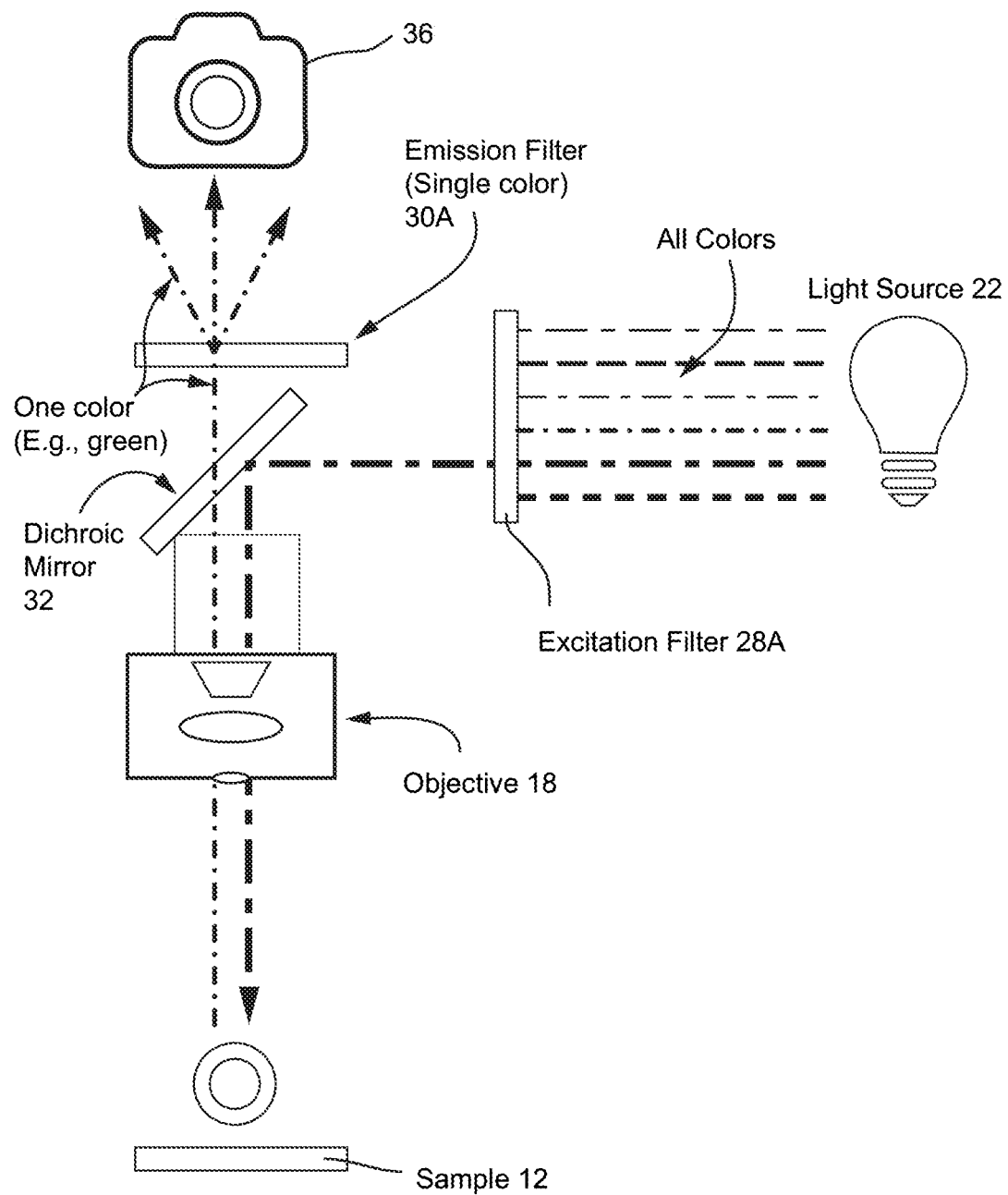
FIG. 3 shows a diagram of a non-limiting example of an epi-fluorescent microscope imaging one fluorophore wavelength, e.g., one color.

FIG. 3 shows a simplified diagram of a non-limiting example of an epi-fluorescent microscope imaging one fluorophore wavelength. In epifluorescence microscopy, both the illuminated and emitted light travels through the same objective lens, where "epi" is borrowed from the Greek to mean "same." The references numerals from FIGS. 1 and 2 carry over with some modification. For example, the image sensor 36 is shown in this example as a camera. The excitation filter 28A narrows the wavelength of incoming light to only those used to excite the sample 12. The dichroic beamsplitter or mirror 32 reflects the excitation light to the sample 12 and simultaneously transmits only the emitted light from the sample 12 back to the camera 36. Both excitation and emission passbands are controlled by the dichroic beamsplitter or mirror 32, which reflects excitation light (shorter wavelengths) via an objective lens 18 onto the sample 12 and passes the resulting emission light (longer wavelengths) through an emission filter 30A that transmits only the wavelengths of the emitted light from the sample 12, in this example only the wavelengths corresponding to the color green, and blocks all the light passed through the excitation filter on to the camera 36.

Figure 4:
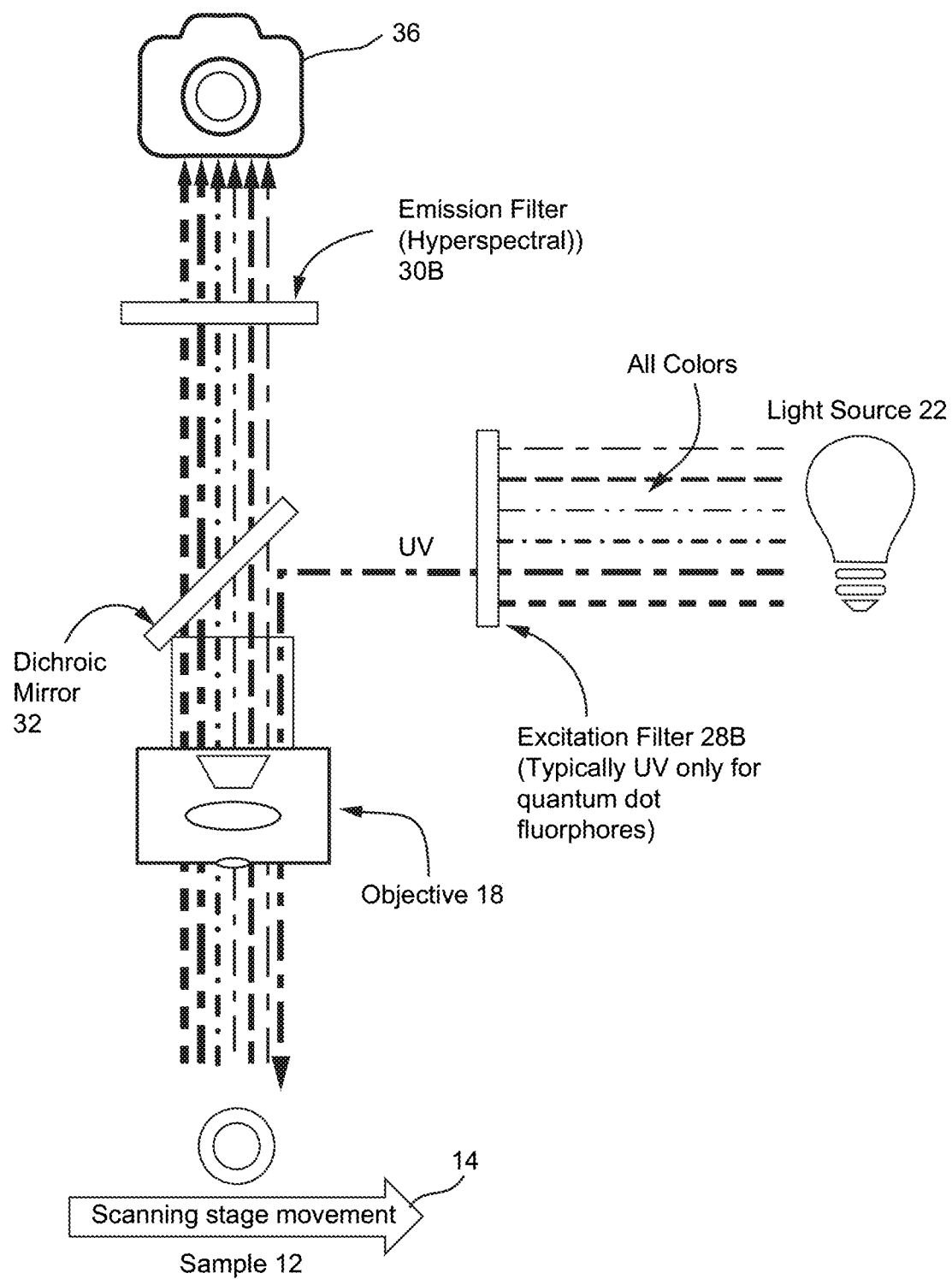
FIG. 4 shows a diagram of a non-limiting example of an epi-fluorescent microscope with a linear variable filter imaging fluorophores that can emit different wavelengths from the same UV excitation, e.g., different colors.

FIG. 4 shows a diagram of a non-limiting example of an epi-fluorescent microscope with a linear variable filter imaging fluorophores that can emit different wavelengths from the same UV excitation. Also, similar to FIG. 3, in this example, the excitation filter 28B only emits UV light which is then reflected onto the sample 12. Fluorophore emission from the sample 12 moved by a scanning stage 14 typically includes several wavelengths in the visible spectrum which is filtered by a linear variable filter 30B before being detected by the camera 36.

Figure 5:
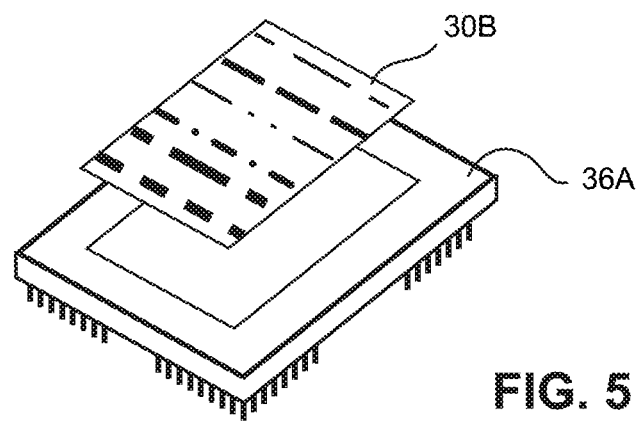
FIG. 5 shows a diagram of an example hyperspectral imaging camera using an optical linear variable bandpass (LVBP) filter in conjunction with a digital camera sensor.

In accordance with an example embodiment, a hyperspectral imaging camera is formed using an optical linear variable bandpass (LVBP) filter 30B in conjunction with a digital camera sensor 36A as shown in FIG. 5. In one non-limiting example, the camera sensor is around 35 mm long by 25 mm wide and includes an array 3,500 pixels by 2,500 pixels. The LVBP filter 30B may span an example range of wavelengths from 400 nm to 750 nm. The LVBP filter 30B bandpass may be for example 10 nm at any point along its length.

Figure 6:
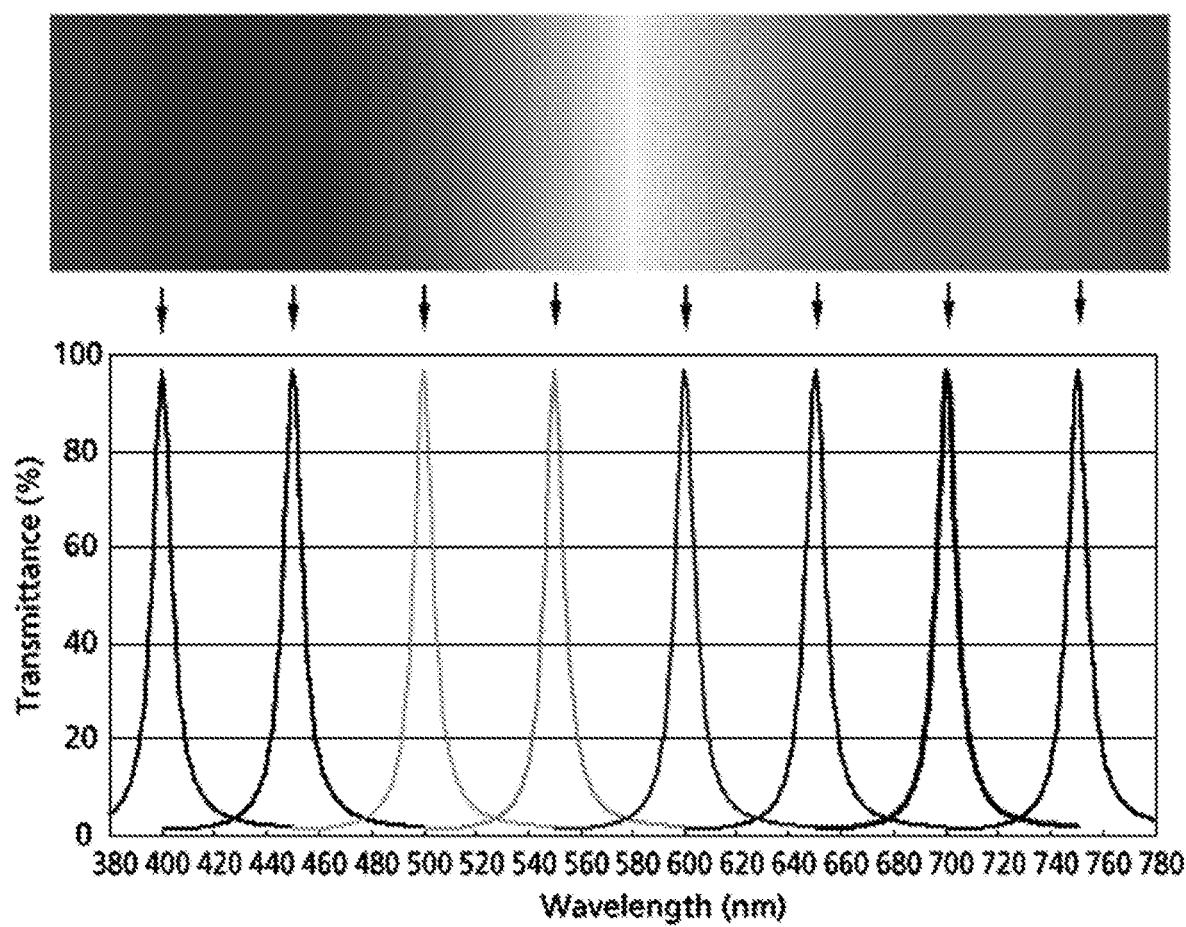
FIG. 6 is graph showing an example bandpass characteristic of an optical linear variable bandpass (LVBP) filter.

FIG. 6 is graph showing an example bandpass characteristic of an optical linear variable bandpass (LVBP) filter measured at eight along its length. Each of the eight band passes represents a different wavelength in the visible spectrum starting with 400 nm at the shortest wavelength shown to 750 nm at the longest wavelength shown. For example, the sample 12 may be treated with different quantum dots which produce a peak luminescent response at different wavelengths in the 400 nm-750 nm range. The sample 12 may be stained with just quantum dots, with quantum dots in combination with conventional organic fluorophores, or just conventional organic fluorophores. It is noted that quantum dots have several important advantages over conventional organic fluorophores. In practice, the quantum dots or other fluorophores are conjugated to an antibody, which is designed to bind to a target in the specimen, such as a protein.

The sample 11 is imaged by the camera 36A to capture images at a plurality of different wavelengths as delineated by the linear variable bandpass filter (LVBP) 30B. The camera 36A may for example take the form of a charge-coupled device imager sensitive to light in a band covering the luminescent response spectra of the fluorophores, e.g., between 400 and 750 nm. Other wavelength ranges may be used.

The camera 36A images the sample 12 at a plurality (M) of discrete wavelengths and responsively generates an image of the sample 12 at each of the M wavelengths. Each of the sample images includes multiple pixels. The imaging wavelengths include wavelengths at which the 1 . . . M fluorophores present in the sample produce a luminescent response to incident light. As an example, the camera (and any attendant spectral filters 30B) is operated so as to capture images of the specimen at 450, 500, 550, 600, 650, and 700 nm. N=6 in this example.

The data resulting from a set of N images of the specimen (one taken at each of the N wavelengths) is referred to as N image data. The N image data is supplied to the computer processing circuitry either within the enclosure 38, e.g., control electronics 40, or is external to the enclosure 38 and the N image data is communicated via a connection, e.g., wired, wireless, optical, network, etc.

Each wavelength that passes through a part of the linear variable bandpass (LVBP) filter 30B reaches a stripe of pixels across the width of the camera sensor. For example, if a given wavelength passes through a region of approximately 1 mm along the filter length, then that wavelength light is detectable by a stripe of 100 pixels long by 2,500 pixels wide in one non-limiting example camera image sensor. Each part of the sample 12 is imaged in (nominally) one wavelength. The whole image frame includes many of these single wavelength stripes collected from different parts of the image. A hyperspectral image of the whole image frame must be created. If the image on the sensor is displaced by (in this example) by about 1 mm, then an adjoining stripe of each wavelength may be collected and stitched (combined) with previously-collected stripe of that wavelength to create a wider image stripe in each wavelength. Also these individual wavelength images begin to overlap the images collected for other wavelengths. By repeating this several times, every wavelength may be collected for one stripe of the image frame. By continuing this stepping process another predetermined number of times, a stripe of every wavelength may be collected over the full image sensor area (the image frame). This set of images may be overlaid with the corresponding displacements to create a full hyperspectral image of the sample.

Optical bandpass filters are manufactured to pass a specific band of optical wavelengths defined by a central wavelength and a width. In the case of a LVBP filter, the central wavelength varies linearly along the length of the filter, (often spanning the visible range as in the examples described above), but the LVBP filter is designed to provide one specific and static pass band width (for example 10 nm) at any point along the LVBP filter length. Once manufactured, the characteristics of the LVBP filter cannot be changed. The pass band width for a LVBP filter must be specified for the manufactured filter, and there is limited choice in selecting this width. It would be advantageous to provide more flexibility in LVBP filters so that different pass band widths may be variably selected rather than a fixed pass band width set at manufacture.

In example embodiments, that flexibility in pass band width for linear variable filters is provided by using two linear variable filters in tandem: one linear variable filter has a linear variable long-pass filter (LVLPF) characteristic and one linear variable filter has a linear variable short-pass filter (LVSPF) characteristic. A long-pass filter has a characteristic cut-off, or edge wavelength and passes all wavelengths longer than the specified edge wavelength. For the LVLPF, the cut-off wavelength varies along the length of the filter, but at each point, the LVLPF passes only all longer wavelengths. The LVSPF has the reciprocal characteristic only passing all wavelengths shorter than the cut-off wavelength. By combining a LVLPF and a LVSPF with a specific overlap, a bandpass filter is formed where the LVLPF blocks shorter wavelengths and the LVSPF blocks longer wavelengths, leaving a pass band. Although the pass band width could be varied by mechanically adjusting the overlap of the filters, this is cumbersome and complex.

Preferred example embodiments employ technology that provides programmably adjustable pass band width using a LVLPF.

Figure 8:
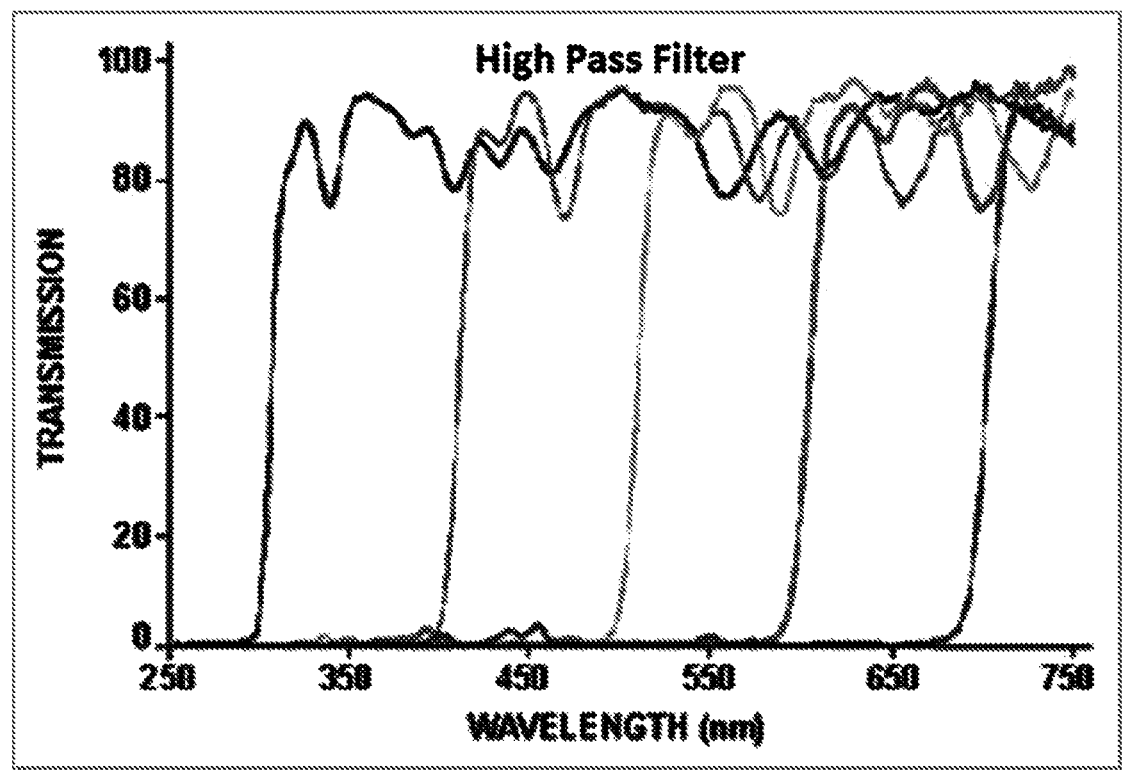
FIG. 8 is a graph showing an example transmission characteristic of a linear variable long-pass filter.

FIG. 8 is a graph showing an example transmission characteristic of a linear variable long-pass filter (LVLPF) at various points long its length. At an initial point along the filter's length, wavelengths greater than about 300 nm are passed. At a next point along the filter's length, wavelengths greater than about 400 nm are passed, then 500 nm, then 600 nm, and then 700 nm.

Figure 9:
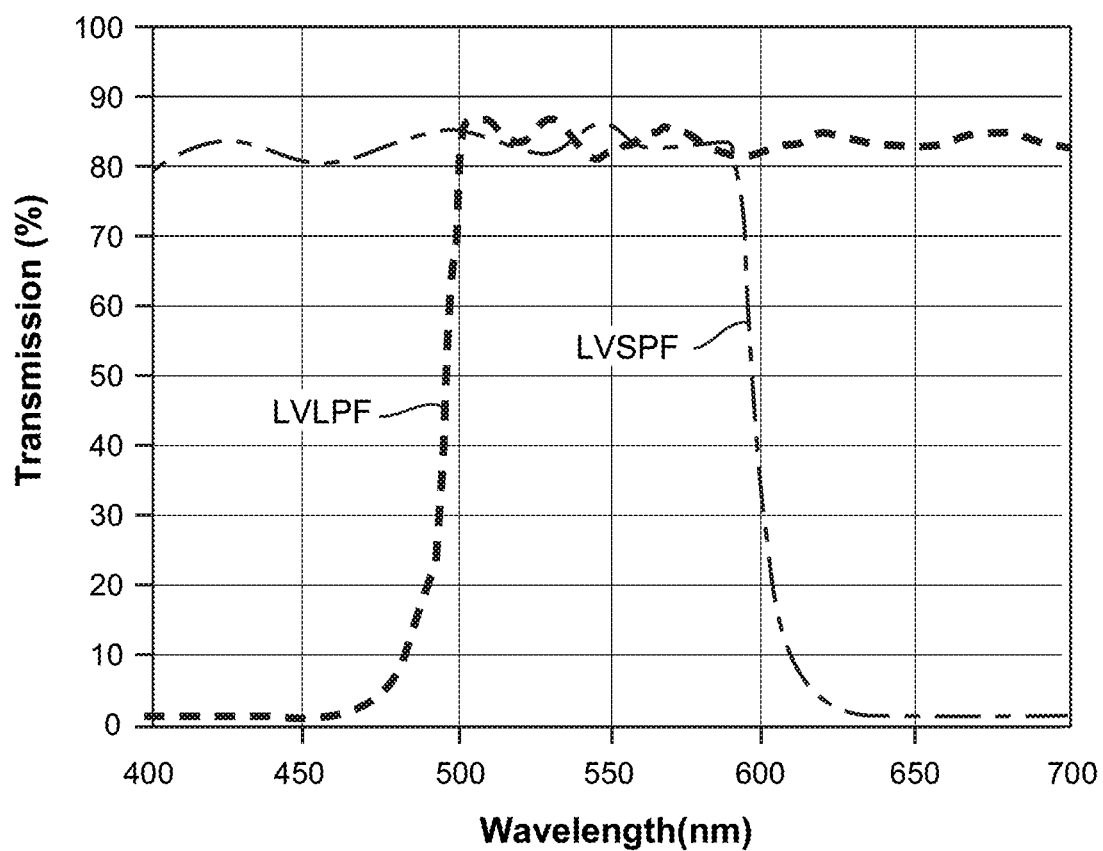
FIG. 9 is a graph showing an example transmission characteristic that shows one point along a linear variable pass band.

FIG. 9 is a graph showing an example transmission characteristic of a linear variable long-pass filter LVLPF and a linear variable short-pass filter LVSPF where the overlap of these two filters defines a pass bandwidth for a linear variable band-pass filter LVBPF. Here, the effective pass band provided by the combined linear variable long-pass and short-pass filters is about 100 nm, i.e., from about 500 nm to about 600 nm.

In many instances, it may not be possible or convenient to specify the optimum pass bandwidth for a filter, and/or mechanical adjustment of overlapping LVLPF and LVSPF filters may not be practical or desired. Example embodiments provide for a more convenient and flexible approach using a computer-configured linear variable band pass filter that can be tailored to provide different programmable or software-directed pass bands directed to each application. While a narrow bandwidth offers good spectral resolution, it also blocks a large portion of the incident light from the camera, resulting lower sensitivity and requiring a longer time to gather an image. A wider pass band allows the camera to collect more light and imaging can be faster, but spectral resolution is less. This resolution-sensitivity trade-off likely changes depending on the application. For example, if a fluorescent microscope is required to resolve four fluorophore wavelengths, then a wider band pass may be used and the resulting imaging speed would be relatively fast, but in another example case, eight, 25, or more wavelengths may need to be resolved, which means speed can be traded off for the required high resolution.

In example embodiments, a linear variable long-pass filter (LVLPF) together with image processing creates a linear variable band pass filter (LVBPF) where a programmable or configurable parameter defines the band pass width. The image processing produces each of several band pass images by subtracting the image information derived from one part of the LVLPF (starting at one wavelength) from the image derived from another part of the LVLPF (starting at another wavelength). In effect, this creates a short pass (or more specifically a high cut) filter in software and the choice of image to be subtracted in each case (i.e., the region of the long-pass filter that is negated or inverted) defines the upper bound of the pass band. The terms subtract and negate include combine, invert, complement, or any other operation that allows the one image data set to be removed from another image data set. A group of different pass bands may be created by selecting different parts of the LVLPF by starting at multiple different wavelengths and/or subtracting from multiple different wavelengths.

While the second, subtracted wavelength band may have a shorter cut-off wavelength than the first waveband, this need not be the case. The subtraction simply means that pixels in the overlap region are negated. Having a negative image for a pass band is another example embodiment. For an example sample spectrum containing wavebands denoted $\lambda 1+\lambda 2+\lambda 3+\lambda 4+\lambda 5$, a first long-pass image including λ3+λ4+λ5 and a second non-overlapping long-pass image containing λ4+λ5 may be collected. Subtracting the second non-overlapping long-pass image from the first non-overlapping long-pass image yields waveband λ3, which forms a regular bandpass filter. In another example case, the first long-pass image may be subtracted from the second long-pass image where the spectral range of the subtracted first image overlaps the second image. This yields the result −λ3, or a negative image of the λ3 waveband, which may be equally useful as a positive image of the λ3 waveband.

In other example embodiments, a linear variable short-pass filter (LVSPF) together with image processing creates a linear variable band pass filter (LVBPF) where a programmable or configurable parameter defines the band pass width. The image processing produces each of several band pass images by subtracting the image information derived from one part of the LVSPF (starting at one wavelength) from the image derived from another part of the LVSPF (starting at another wavelength). In effect, this creates a filter in software, and the choice of image to be subtracted in each case (i.e., the region of the short-pass filter that is negated or inverted) defines the longer boundary of the pass band. The terms subtract and negate include combine, invert, complement, or any other operation that allows the one image data set to be removed from another image data set. A group of different pass bands may be created by selecting different parts of the LVSPF by starting at multiple different wavelengths and/or subtracting from multiple different wavelengths. Having a positive and/or negative images for pass bands are, as described above, example embodiments.

For ease of description, the following description of features and embodiments assumes an adaptively configurable-LVLPF, but it is understood that similar features and embodiments may be analogously implemented for an adaptively configurable-LVSPF.

Figure 10:
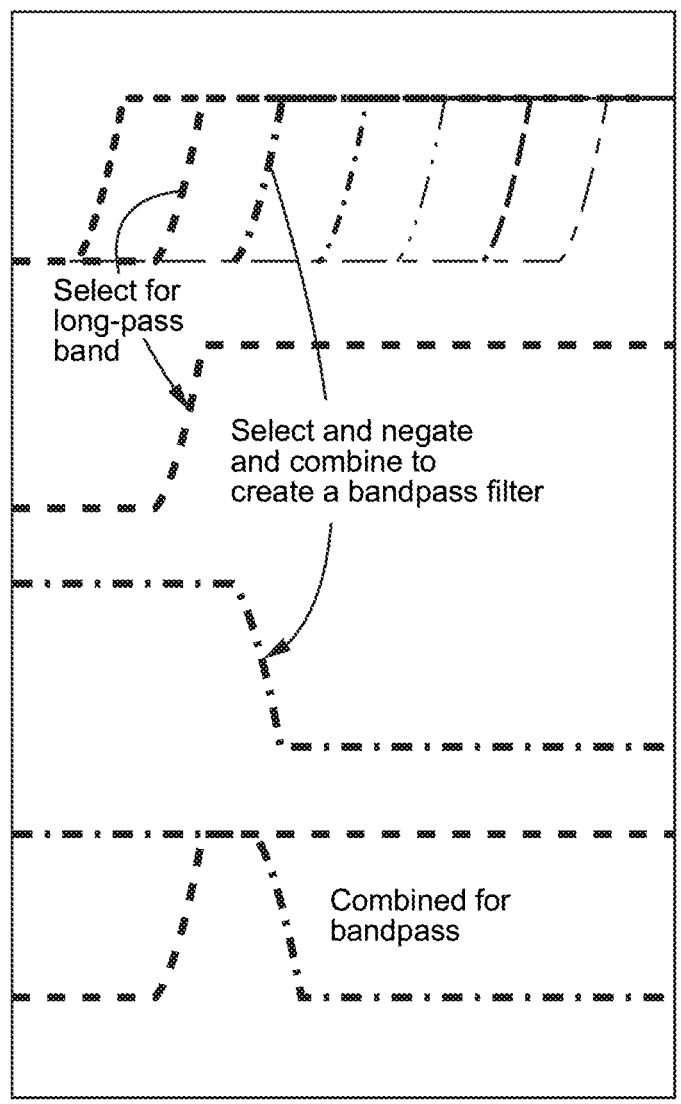
FIG. 10 is a diagram illustrating a filter used to create different long-pass images and shows subtracting one long-pass image from another to create a bandpass filter.

FIG. 10 is a diagram illustrating a configurable linear variable long-pass filter used to generate different band pass images by a computer (e.g., as a part of the control electronics 40 or external computer processing) subtracting pixel values for a second long-pass image from pixel values for a first long-pass image, where both sets of image data (pixel values) are obtained by the way a linear variable long-pass filter. The offset between selected long and negated or inverted long pass image data sets, and thus the band pass width, is determined by one or more band width selection parameters, which may be chosen by a user input to the computer or by the application and set for the image processing. This band width selection parameter(s) may be stored in memory accessible by or within the control electronics 40 or external computer processing. Accordingly, the computer may select any two of the available LVLPF bands, collect a first and a second set of image data corresponding to the selected LVLPF bands, negate or invert the second set of image data, and combine the first and the negated or inverted second sets of image data to produce an LVBPF tailored to the specific needs of an application and/or the particular requirements of a user. If the needs change, then the band width selection parameter(s) is/are readily modified to accommodate the change, and a "new" LVBPF is configured.

Figure 7:
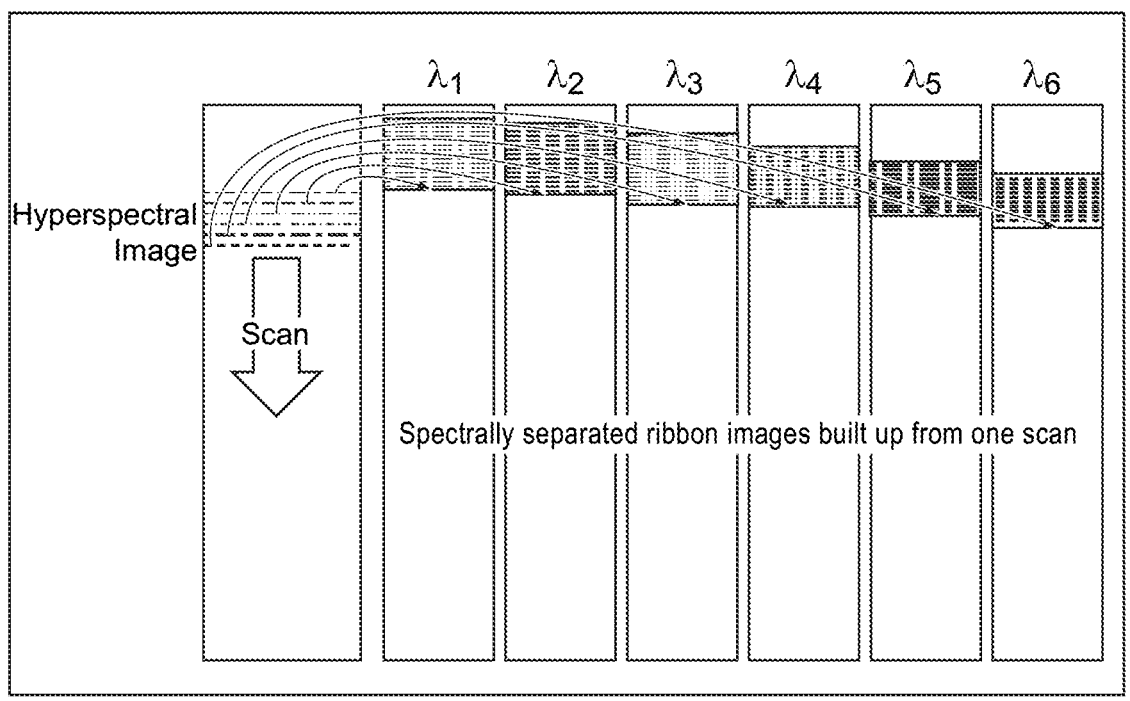
FIG. 7 shows an example of a hyperspectral imaging technique for six wavelengths using a hyperspectral imaging camera using a linear variable filter.
Figure 11:
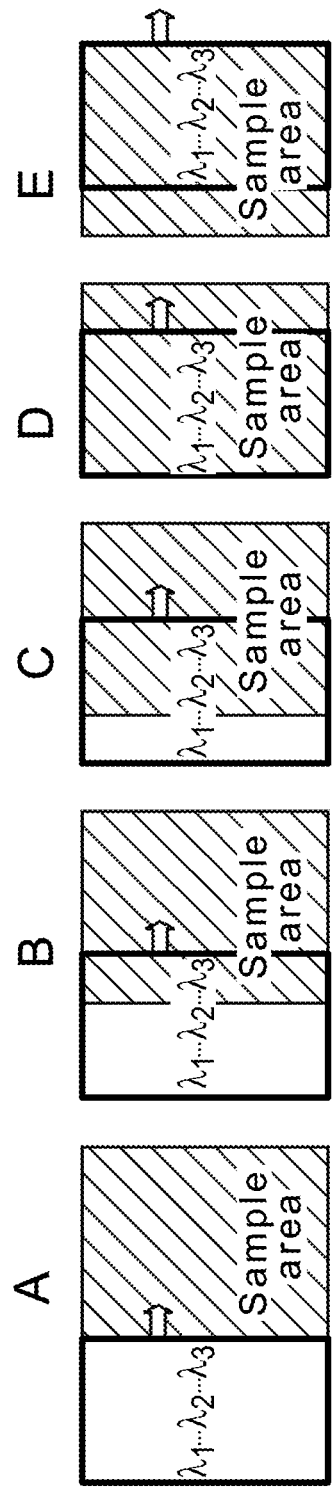
FIG. 11 is a diagram illustrating an example of stepping along one axis to build a full hyperspectral long-pass image.

Example procedures for collecting and building image data using a LVLPF are now described. FIG. 11 is a diagram illustrating an example of stepping a camera imaging sensor along one axis across a sample area to build a hyperspectral image of the sample area. In this example, the camera imaging sensor is divided into three portions defined by an example linear variable filter with the three scan portions labelled λ1, λ2, and λ3 identifying three different wavelengths, e.g., three different colors. In practice, the linear variable filter covers a continuum of wavelengths. Each step along the horizontal axis moves the camera with three scan portions λ1, λ2, and λ3 from the left of the sample area, onto the sample area, across the sample area, and then off of the sample area in stepping stages A-E. In step B, a portion of the sample area is imaged in wavelength λ3 only. In step C, this same portion of the sample area is imaged in wavelength λ2 only. Also in step C, the second portion of the sample area is imaged with λ3, and the corresponding image portion is stitched to (or combined with) the λ3 image of the first portion of the sample, thereby beginning to create a more complete image of the sample area for λ3. FIG. 7 shows an example of stitching image portions for each of multiple wavelengths. In step D, the first portion of the sample area is imaged in wavelength λ1, which completes imaging of this portion of the sample. The steps continue until step E where all portions of the sample area have been imaged in all wavelengths λ1, λ2, and λ3, and all of the partial images are stitched (combined) together to form complete images of the sample area in all wavelengths λ1, λ2, and λ3.

Figure 12:
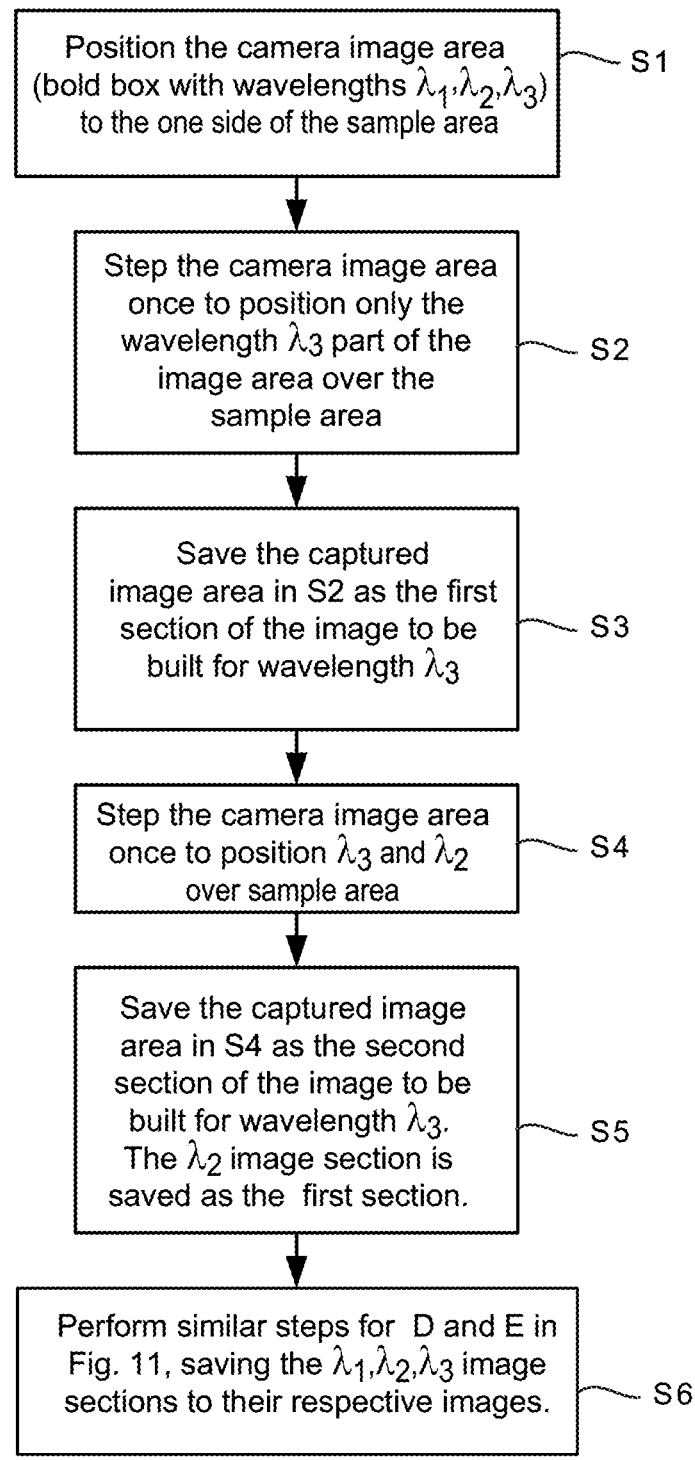
FIG. 12 is a flowchart diagram illustrating example procedures for generating a set of hyperspectral long-pass images.

FIG. 12 is a flowchart diagram illustrating example procedures for generating a hyperspectral image of a sample area that is formed from N individual scan portion images, where N is a positive integer having values in the range of 4 to 25 or greater. In the example in FIG. 11, N=3. These scan portion images cover separate spectral regions which could be band pass images, long-pass images, short pass images, etc. For long-pass images, each of the N individual image portions have a unique cut-off wavelength. FIG. 12 uses the example from FIG. 11 for illustration purposes only but is applicable to other values of N. In step S1, the entire camera image capture area is initially positioned to the left of the sample area. In step S2, the camera image area is stepped using a motorized stage or other suitable scanning mechanism once to position only the λ3 imaging area portion over the sample area. The captured λ3 image area data is saved as a first section (ribbon) of the sample image to be built for the λ3 wavelength (step S3). The camera is stepped to position both the λ2 and λ3 scan image sections over the sample area (step S4). The captured λ3 image area is saved as the second section of the image of the sample area to be built for and combined with the first section of the image of the sample area for the λ3 wavelength. The λ2 image portion is saved as the first section of the image of the sample area for the λ2 wavelength image (step S5). Similar procedures are performed to obtain the λ1, λ2, and λ3 scan image portions over the entire sample area saving the λ3, λ2, and λ1 image sections to their respective images of the sample area until the last λ1 section is collected, stitched, and saved (step S6).

Figure 13:
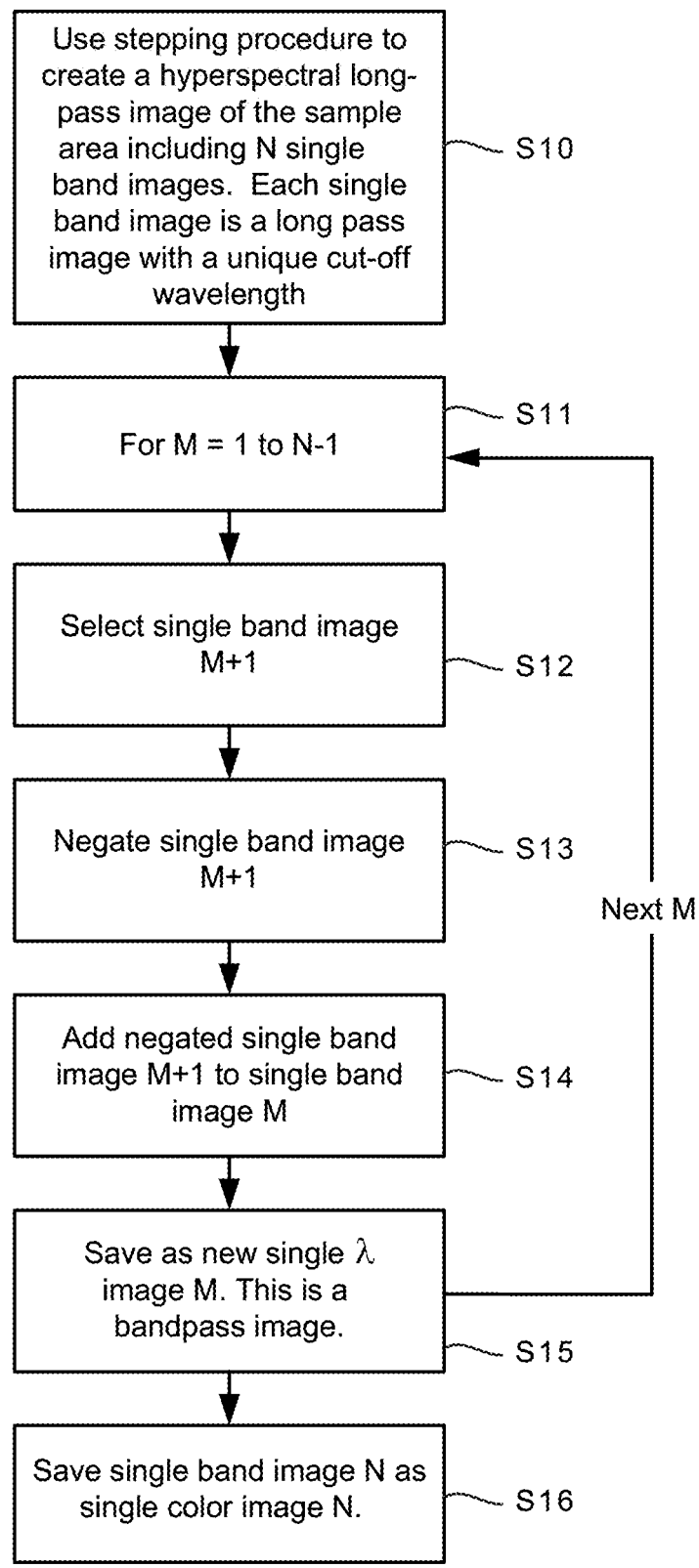
FIG. 13 is a flowchart diagram illustrating example procedures for converting N long-pass images to bandpass images by subtracting long-pass images.

FIG. 13 is a flowchart diagram illustrating example procedures for converting N long pass images (N is the number of wavelength bands collected) of the sample area to band pass images by subtracting long-pass images as described above with respect to FIG. 10. A stepping procedure like that described in FIGS. 11 and 12 is used to create a hyperspectral long-pass image data set of the sample area that includes N single wavelength or frequency band image data sets, e.g., λ1, λ2, and λ3 image data sets of the sample area. Each single wavelength or frequency band image is a long-pass image with a unique cut off wavelength (step S10). Step S11 is the start of a loop, where M (the index)=1 to N−1. A single wavelength or frequency band image M+1 is selected (step S12). The single wavelength or frequency band image M+1 data is negated (step S13). The negated single wavelength or frequency band image M+1 is added to the single wavelength or frequency band image M (step S14). The result is saved as a new single wavelength image M data set corresponding to a desired band pass image (step S15). If only one pass band is needed, then the process may end here. However, if multiple pass bands are desired, then control returns to step S11 for the next value of M, if M is less that N−1. If M=N−1, then the remaining single wavelength or frequency band image N is saved as the single wavelength image N as there is no further image data set to be subtracted (step S16). The result is a hyperspectral image that includes a set of different pass band images. For example, if three long pass band cut offs correspond to 400 nm, 500 nm, and 600 nm, then after subtracting, the result is three pass bands of red, green, and blue colors.

To emulate a LVBPF of arbitrary bandwidth, a whole collection of images of equally-spaced, equal-width pass bands across the spectrum may be generated in similar fashion. Some applications may not require all of these bands, and in that case, only specific bands, perhaps each of specific bandwidth may be generated. For example, the long pass cut-offs needed may be determined by the physical/spatial offset of the camera at the time of imaging, and only those required images are collected. If the application is to image a certain set of fluorophores, then the process may be tailored to just those particular emission spectra of those fluorophores, each having a nominal wavelength and band width.

One valuable example application for hyperspectral imaging using the technology described above is in fluorescence microscopy described earlier in this application. Image sizes in fluorescence microscopy are limited by the geometry of the microscope, e.g., most microscopes typically have a 25 mm diameter tube. A typical microscope camera has an image sensor having an area of around 13 mm by 13 mm, or a diagonal of nearly 19 mm, which fits well within the typical 25 mm maximum image diameter. A problem is that the typical LVBP center wavelength varies by about 10 nm per mm of length. This rate of change per unit length is close to current practical limits for manufacture of a high quality linear variable filter. As a result, it is not currently possible to make a high quality linear variable bandpass filter covering the visible spectrum in the 13 mm length of the typical microscope image sensor.

However, in further example embodiments, a longer length linear variable bandpass filter, e.g., 35 mm long, is partitioned into a shorter lengths, or sections, each of these sections to fit a shorter length, e.g., 13 mm, camera sensor. But this shorter section of the linear variable bandpass filter can only span a portion (e.g., roughly one third) of the visible spectrum. As a result, multiple ones of the shorter filter sections, e.g., three 13 mm sections, can be cut from longer, e.g., 35 mm, linear variable bandpass filters to make a set of three spectrally overlapping sections, for example spanning wavelength ranges 400 to 530 nm, 510 to 640 nm, and 620 to 750 nm, which together may span all of a desired spectrum.

Figures 14A, 14B:
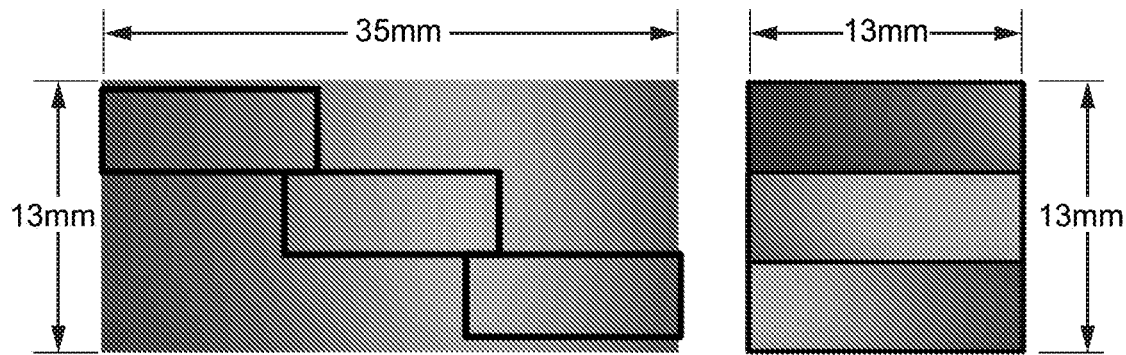
FIGS. 14A and 14B are diagrams illustrating an example embodiment where a standard linear variable filter is partitioned into three shorter portions, which together span the whole length of the LVBPF, but which may be configured into a partitioned LVBPF that fits into a standard microscope tube.

FIGS. 14A and 14B are diagrams illustrating an example embodiment where an example LVBPF dimensioned 13 mm by 35 mm in FIG. 14A is partitioned into shorter 13 mm sections and configured into a partitioned LVBP in FIG. 14B that fits a standard microscope tube. These figures show for this example how these sections may be divided and assembled into a 13 mm×13 mm LVBP filter. Since these multiple filter sections may total to more than the LVBP filter length, e.g., 35 mm, the LVBP filter sections may be chosen to have a small spectral overlap. This overlap is useful for avoiding complications associated with collecting images spanning the discontinuous region around the cut/edge of each section.

Like the original LVBP filter, the partitioned LVBP filter comprises optical pass band sections spanning the same visible spectrum. Each section has the same bandwidth, e.g., 10 nm, as the original LVBP filter. However, each section is only a fraction, e.g., one-third, of the width of the camera sensor instead of the full width. An example camera sensor may comprise an array of 2048 by 2048 pixels, where a single wavelength illuminates an area of the sensor approximately 154 pixels long by 682 pixels wide. In practice for this example, the edges of these regions will have image imperfections, and the useable width from each filter section is likely to be less than 682 pixels wide.

One image taken using a partitioned LVBP filter like the example shown in FIG. 14B captures a small region of the sample area in each wavelength. As a result, creating a full hyperspectral image over of the full camera sensor area is more involved for a partitioned LVBP filter than described in conjunction with by FIGS. 11 and 12 using a non-partitioned LVBP filter. The positon of the sample area image on the camera image sensor is stepped length-wise as described in conjunction with FIG. 11, but this only builds a wavelength or frequency band of the sample area from one third of the image sensor width (or a little less than one third to avoid edge discontinuities). Thus, the camera image sensor is also stepped width-wise to collect multiple length-wise bands of the sample area. For the example in FIGS. 14A and 14B, 3 width-wise steps are required.

Figure 15:
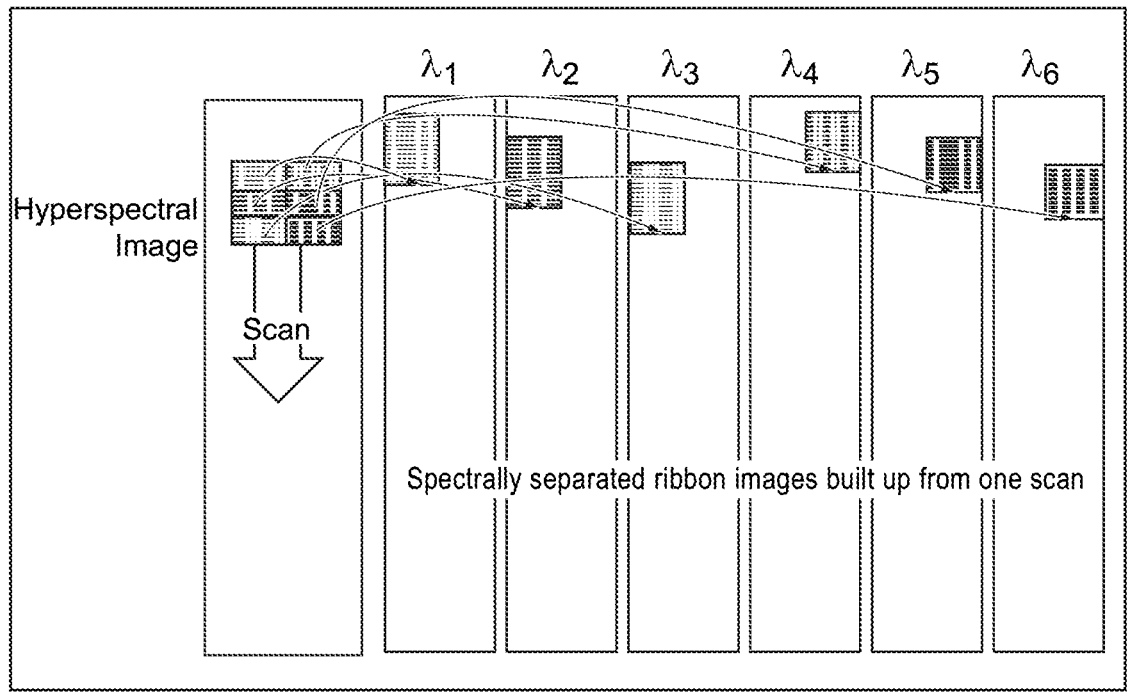
FIG. 15 is a diagram illustrating an example embodiment of a hyperspectral scan using a partitioned LVBPF that is partitioned into two parts rather than three parts as in FIGS. 14A and 14B.

A sample area is imaged using length-wise and width-wise steps to cover a 2-dimensional area of the sample. FIG. 15 is a diagram illustrating an example embodiment of a hyperspectral scan for six example wavelength bands $\lambda 1$-$\lambda 6$ using a LVBPF partitioned into two sections, similar to the filter shown in FIG. 14B. The sample area is moved beneath the camera/LVBP filter, and image portions for each single wavelength image are taken and stitched into (added to) images of the sample area for each of the single wavelengths. The result of stepping length-wise over the sample is a continuous image (composed of many small images stitched together) in each wavelength, but the images from one filter section are not from the same region of the sample as from the other filter section. It is therefore necessary to step width-wise and repeat the length-wise stepping process to build up a complete image set in all wavelengths $\lambda 1$-$\lambda 6$.

Figure 16:
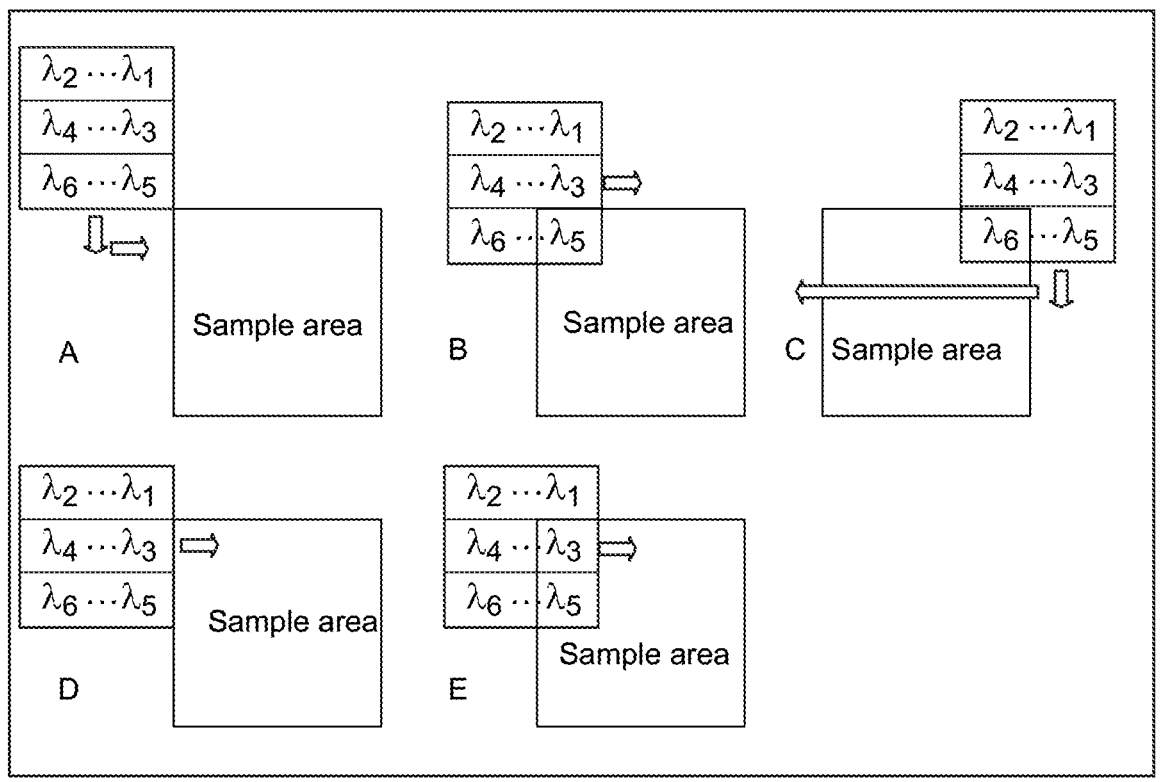
FIG. 16 is a diagram illustrating an example embodiment building on FIG. 15 to step along two axes to create a full hyperspectral image with a partitioned LVBP like the one shown in FIG. 14.

FIG. 16 is a diagram illustrating an example embodiment to step along two axes to create a full hyperspectral image with a partitioned LVBPF like the example shown in FIG. 14B. This figure is similar in some respects to FIG. 11, but rather than three wavelength areas as in FIG. 11, there are six wavelength areas $\lambda 1$ to $\lambda 6$. At step A, the camera image area with the nine wavelength areas is positioned at the upper left corner of the sample area. At step B, the camera image area is stepped down and to the right one step so that the $\lambda 5$ area overlaps some of the sample area, and an image portion is captured for $\lambda 5$. The lower row of the camera image area including wavelength areas $\lambda 6$ and $\lambda 5$, is stepped across the sample area, and an image is captured at each step until only the $\lambda 6$ area overlaps the sample area. At step C, the camera image area moves down one area and increments back to the left to start the next row of images including wavelength areas $\lambda 4$ and $\lambda 3$ at step D. At step E, the camera image area is stepped to the right one step so that the $\lambda 3$ and $\lambda 5$ areas overlap some of the sample area, and an image portion is captured for $\lambda 3$ and $\lambda 5$. This process repeats until only $\lambda 2$ overlaps the sample area and imaging and stitching are completed for the entire sample area for all the wavelengths λ1-λ6.

Figure 17:
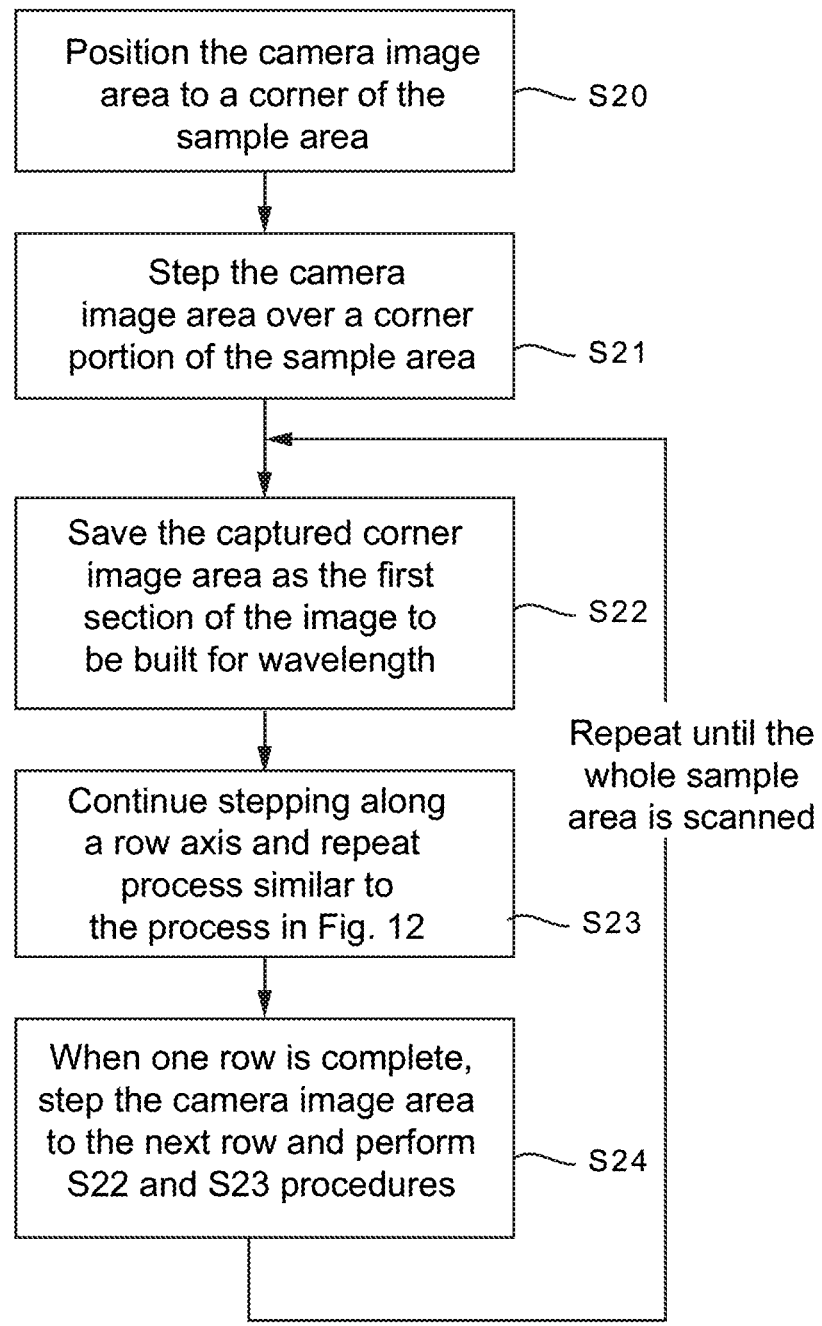
FIG. 17 is a flowchart diagram illustrating example procedures for scanning a sample using a partitioned LVBP filter and the two axis stepping approach of FIG. 16 to generate a hyperspectral image.

FIG. 17 is a flowchart diagram illustrating example procedures for scanning a sample using a partitioned LVBPF and the two axis stepping approach of FIG. 16 to generate a hyperspectral image. At step S20, the camera image area is positioned next to the sample area. The camera image area is stepped once to the right and once downwards to position the λ5 image area over the sample area (step S21). The captured λ5 image area is saved as the first part of the image to be built for a λ5 wavelength (step S22). The camera image area is continued to be stepped to the right as for the process described for FIG. 11 (step S23). When each row is completed, the camera image area is stepped down and back to the left to perform another pass over the sample area (step S24). Procedures S23 and S24 repeat until the entire sample area is scanned by every one of the wavelength image areas. When the scanning and stitching for each wavelength is complete, there is a full image for each wavelength passed by the LVBF that are combined to form one hyperspectral image of the sample area.

The image sensor scans or steps over the whole same area, and scan data is collected for as many wavelength channels as required. Filtering and processing procedures may be performed on the image data, e.g., filtering, subtraction, correlation, and/or thresholding of the image data depending on the example embodiment, to detect cells and/or cell fragments, more generally cell objects. Peak height, peak location, and/or area (number of adjoining pixels) above a threshold are examples of parameter information that may be retained from each image for each wavelength channel scanned. Methods and apparatus for capture, analysis, aggregation, and output of detected cancer cells or fragments are described in commonly-assigned PCT patent application number, PCT/US2014/071292, filed on Dec. 18, 2014, and PCT/US2016/060010, filed on Nov. 2, 2016, the contents of both of which are incorporated herein by reference.

For example, data processing circuitry in an optical/image fluorescence processing system detects, from selected image data, marked objects in the sample, determines one or more parameters associated with a detected marked object, and generates coordinate locations of detected marked objects in the sample. Marked objects in the sample, e.g., quantum dot fluorophores, organic fluorophores, or autofluorescence, may be detected by the optical/image fluorescence processing system, and one or more parameters associated with one or more of the detected marked objects determined. Coordinate locations of detected marked objects in the sample may also be determined and used for further imaging and/or processing of images of the marked objects.

The affinity molecule, in non-limiting examples, is an antibody, bacteriophage, scaffold protein, aptamer, lectin, peptide, engineered polypeptide mimetic or small molecule designed to target specific objects or specific components of objects for detection.

The object detected, in non-limiting examples, could be rare cells such as circulating tumor cells, circulating stem cells, circulating fetal cells, circulating endothelial cells, circulating cancer associated fibroblasts, circulating cancer associated macrophages, or organisms in a biome, pathogen contaminants in biological samples or food and water supplies.

Autofluorescence of the object could be used, in non-limiting examples, to detect the biological and non-biological objects of interest in food and water contamination, during chemical processes, during oil processing, or during multiple manufacturing processes.

The sample format, in non-limiting examples, includes a microscope slide onto which the sample is applied, a microtiter plate, a filter, an ELISA strip, a lateral flow strip or microarray.

Although the present disclosure has been described with reference to particular example embodiments, it will be appreciated by those skilled in the art that the disclosure may be embodied in many other forms.

All methods described herein can be performed in any suitable order unless otherwise indicated herein. The use of any and all examples, or example language (e.g., "such as") provided herein, is intended merely to better illuminate the example embodiments and does not pose a limitation on the scope of the claims appended hereto unless otherwise claimed. No language or terminology in this specification should be construed as indicating any non-claimed element as essential or critical.

Throughout this specification, unless the context requires otherwise, the word "comprise", or variations such as "comprises" or "comprising, "including," "containing," and the like will be understood to imply the inclusion of a stated element or integer or group of elements or integers but not the exclusion of any other element or integer or group of elements or integers.

As used herein, the singular forms "a," "an," and "the" may also refer to plural articles, i.e., "one or more," "at least one," etc., unless specifically stated otherwise. For example, the term "a fluorophore" includes one or more fluorophores.

Recitation of ranges of values herein are merely intended to serve as a shorthand method of referring individually to each separate value falling within the range, unless otherwise indicated herein, and each separate value is incorporated into the specification as if it were individually recited herein. Where a specific range of values is provided, it is understood that each intervening value, to the tenth of the unit of the lower limit unless the context clearly dictates otherwise, between the upper and lower limit of that range and any other stated or intervening value in that stated range, is included therein. All smaller subranges are also included. The upper and lower limits of these smaller ranges are also included therein, subject to any specifically excluded limit in the stated range.

The term "about" or "approximately" means an acceptable error for a particular recited value, which depends in part on how the value is measured or determined. In certain embodiments, "about" can mean 1 or more standard deviations. When the antecedent term "about" is applied to a recited range or value it denotes an approximation within the deviation in the range or value known or expected in the art from the measurements method. For removal of doubt, it shall be understood that any range stated herein that does not specifically recite the term "about" before the range or before any value within the stated range inherently includes such term to encompass the approximation within the deviation noted above.

The invention claimed is:

1. An imaging system for imaging a sample, comprising:
 a light source to illuminate a sample with one or more wavelengths of light;
 an image sensor to detect light from the illuminated sample;
 a linear variable long pass filter positioned to filter light reflected from the sample to pass to the image sensor multiple different wavelength bands having different cut-off wavelengths, where wavelengths of light on one side of a cut-off wavelength are blocked and wavelengths of light on the other side of the cut-off wavelength are passed as multiple different long pass wavelength bands for detection by the image sensor;

the image sensor configured to detect light for each of the multiple different long pass wavelength bands from the sample, and data processing circuitry configured to:
convert the detected light for the multiple different long pass wavelength bands for the sample into corresponding different long pass wavelength band data sets for the sample;

dynamically select a first one of the long pass wavelength band data sets having a first cut-off wavelength and a second different one of the long pass wavelength band data sets having a second different cut-off wavelength;

negate values of the second long pass wavelength band data set;

combine the first long pass wavelength band data set and the negated second long pass wavelength band data set to generate a first pass band that selects image data from the sample with wavelengths between the first and second cut-off wavelengths; and process the selected image data in the first pass band to identify marked objects in the sample, wherein the data processing circuitry is further configured to select a different one of the first or second of the long pass wavelength band data sets having a different first or second cut-off wavelength and to generate therefrom a second pass band different from the first pass band, select image data from the sample with wavelengths in the second pass band, and process the selected image data in the second pass band to identify marked objects in the sample.

2. The imaging system as in claim 1, wherein light is ultraviolet light to illuminate quantum dot fluorophores present in the sample.

3. The imaging system as in claim 1, wherein the data processing circuitry is configured to select the first long pass wavelength band data set and the second long pass wavelength band data set based on one or more configurable parameters that are selectable during operation of the imaging system.

4. The imaging system as in claim 1, wherein the data processing circuitry is configured to:
select a third one of the long pass wavelength band data sets having a third cut-off wavelength and a fourth different one of the long pass wavelength band data sets having a fourth different cut-off wavelength;

negate values of the fourth long pass wavelength band data set;

combine the third long pass wavelength band data set and the negated fourth long pass wavelength band data set to generate the second pass band that selects image data from the sample with wavelengths between the third and fourth cut-off wavelengths;

select a fifth one of the long pass wavelength band data sets having a fifth cut-off wavelength and a sixth different one of the long pass wavelength band data sets having a sixth different cut-off wavelength;

negate values of the sixth long pass wavelength band data set;

combine the fifth long pass wavelength band data set and the negated sixth long pass wavelength band data set to generate a third pass band that selects image data from the sample with wavelengths between the fifth and sixth cut-off wavelengths; and process the selected image data in the third pass band to identify marked objects in the sample, wherein the data processing circuitry is configured to select the first, second, third, fourth, fifth, and sixth long pass wavelength band data sets based on one or more configurable parameters during operation of the imaging system, and wherein the first, second, and third pass bands implement a linear variable band pass filter.

5. The imaging system as in claim 1, further comprising a scanning mechanism to allow the image sensor to detect light for each of the multiple different long pass wavelength bands from the sample, wherein the scanning mechanism is configured to move the sample relative to the image sensor, and wherein the data processing circuitry is configured to collect and store in memory portions of image data of the sample for each wavelength band, and at the end of the scan of the sample, combine the stored portions of image data for each wavelength band to produce a hyperspectral image data set for the sample.

6. The imaging system as in claim 1, further comprising a scanning mechanism to allow the image sensor to detect light for each of the multiple different long pass wavelength bands from the sample, wherein:
the sample is divided into multiple areas,
the scanning mechanism is configured to move the sample relative to the image sensor both length-wise and width-wise to permit the data processing circuitry to collect and store in memory portions of image data of the sample for each wavelength band to generate a set of images in each of the wavelength bands for each of the multiple areas of the sample, and for each area of the sample, the data processing circuitry is configured to process the set of wavelength band images to generate a set of bandpass images and to combine the bandpass images to produce a hyperspectral image data set for all the areas of sample.

7. The imaging system as in claim 1, wherein the data processing circuitry is configured to:
detect, from the selected image data, marked objects in the sample, determine one or more parameters associated with a detected marked object, and generate coordinate locations of detected marked objects in the sample.

8. The imaging system as in claim 1, wherein an affinity molecule binds to objects present in the sample, and wherein the affinity molecule is one of an antibody, bacteriophage, scaffold protein, aptamer, lectin, peptide, engineered polypeptide mimetic, or small molecule designed to target specific objects or specific components of objects for detection.

9. The imaging system as in claim 1, wherein the marked objects in the sample include (i) rare cells including circulating tumor cells, circulating stem cells, circulating fetal cells, circulating endothelial cells, circulating cancer associated fibroblasts, circulating cancer associated macrophages, (ii) organisms in a biome, or (iii) pathogen contaminants in biological samples or food and water supplies, or wherein the marked objects in the sample include biological and non-biological objects in food or water, or wherein the marked objects in the sample include objects detected during chemical processes, oil processing, or a manufacturing process.

10. The imaging system as in claim 1, wherein the sample is on or in:
a microscope slide, a microtiter plate, a filter, an enzyme-linked immunosorbent assay (ELISA) strip, a lateral flow strip, or a microarray.

11. An imaging system for imaging a sample across one or more wavelengths, comprising:
a light source to illuminate a sample with one or more wavelengths of light;
an image sensor to detect light from the illuminated sample;
a linear variable short pass filter positioned to filter light reflected from the sample to pass to the image sensor multiple different wavelength bands having different cut-off wavelengths, where wavelengths of light on one side of a cut-off wavelength are blocked and wavelengths of light on the other side of the cut-off wavelength are passed as multiple different short pass wavelength bands for detection by the image sensor;
the image sensor configured to detect light for each of the multiple different short pass wavelength bands from the sample, and
data processing circuitry configured to:
convert the detected light for the multiple different short pass wavelength bands for the sample into corresponding different short pass wavelength band data sets for the sample;
dynamically select a first one of the short pass wavelength band data sets having a first cut-off wavelength and a second different one of the short pass wavelength band data sets having a second different cut-off wavelength;
negate values of the second short pass wavelength band data set;
combine the first short pass wavelength band data set and the negated second short pass wavelength band data set to generate a first pass band that selects image data from the sample with wavelengths between the first and second cut-off wavelengths; and
process the selected image data in the first pass band to identify marked objects in the sample,
wherein the data processing circuitry is further configured to select a different one of the first or second of the short pass wavelength band data sets having a different first or second cut-off wavelength and to generate therefrom a second pass band different from the first pass band, select image data from the sample with wavelengths in the second pass band, and process the selected image data in the second pass band to identify marked objects in the sample.

12. The imaging system as in claim 11, wherein the data processing circuitry is configured to select the first short pass wavelength band data set and the second short pass wavelength band data set based on one or more configurable parameters that are selectable during operation of the imaging system.

13. The imaging system as in claim 11, wherein the data processing circuitry is configured to:
select a third one of the short pass wavelength band data sets having a third cut-off wavelength and a fourth different one of the short pass wavelength band data sets having a fourth different cut-off wavelength;
negate values of the fourth short pass wavelength band data set;
combine the third short pass wavelength band data set and the negated fourth short pass wavelength band data set to generate the second pass band that selects image data from the sample with wavelengths between the third and fourth cut-off wavelengths;
select a fifth one of the short pass wavelength band data sets having a fifth cut-off wavelength and a sixth different one of the short pass wavelength band data sets having a sixth different cut-off wavelength;
negate values of the sixth short pass wavelength band data set;
combine the fifth short pass wavelength band data set and the negated sixth short pass wavelength band data set to generate a third pass band that selects image data from the sample with wavelengths between the fifth and sixth cut-off wavelengths; and
process the selected image data in the third pass band to identify marked objects in the sample;
wherein the data processing circuitry is configured to select the first, second, third, fourth, fifth, and sixth short pass wavelength band data sets based on one or more configurable parameters during operation of the imaging system; and
wherein the first, second, and third pass bands implement a linear variable band pass filter.

14. The imaging system as in claim 11, further comprising a scanning mechanism to allow the image sensor to detect light for each of the multiple different short pass wavelength bands from the sample,
wherein the scanning mechanism is configured to move the sample relative to the image sensor, and wherein the data processing circuitry is configured to collect and store in memory portions of image data of the sample for each wavelength band, and at the end of the scan of the sample, combine the stored portions of image data for each wavelength band to produce a hyperspectral image data set for the sample.

15. The imaging system as in claim 11, further comprising a scanning mechanism to allow the image sensor to detect light for each of the multiple different short pass wavelength bands from the sample,
wherein the data processing circuitry is configured to:
detect, from the selected image data, marked objects in the sample,
determine one or more parameters associated with a detected marked object, and
generate coordinate locations of detected marked objects in the sample.

16. The imaging system as in claim 11, wherein an affinity molecule binds to objects present in the sample, and wherein the affinity molecule is one of an antibody, bacteriophage, scaffold protein, aptamer, lectin, peptide, engineered polypeptide mimetic, or small molecule designed to target specific objects or specific components of objects for detection.

17. The imaging system as in claim 11, wherein the marked objects in the sample include (i) rare cells including circulating tumor cells, circulating stem cells, circulating fetal cells, circulating endothelial cells, circulating cancer associated fibroblasts, circulating cancer associated macrophages, (ii) organisms in a biome, or (iii) pathogen contaminants in biological samples or food and water supplies, or wherein the marked objects in the sample include biological and non-biological objects in food or water, or wherein the marked objects in the sample include objects detected during chemical processes, oil processing, or a manufacturing process.

18. The imaging system as in claim 11, wherein the sample is on or in:

a microscope slide, a microtiter plate, a filter, an enzyme-linked immunosorbent assay (ELISA) strip, a lateral flow strip, or a microarray.

19. A method for imaging a sample, comprising:
illuminating a sample with one or more wavelengths of light;
detecting with an image sensor light from the illuminated sample;
filtering with a linear variable long pass filter light reflected from the sample to pass to the image sensor multiple different wavelength bands having different cut-off wavelengths, where wavelengths of light on one side of the cut-off wavelength are blocked and wavelengths of light on the other side of the cut-off wavelength are passed as multiple different long pass wavelength bands for detection by the image sensor;
the image sensor detecting light for each of the multiple different long pass wavelength bands from the sample;
converting the detected light for the multiple different long pass wavelength bands for the sample into corresponding different long pass wavelength band data sets for the sample;
dynamically selecting during operation of the imaging system a first one of the long pass wavelength band data sets having a first cut-off wavelength and a second different one of the long pass wavelength band data sets having a second different cut-off wavelength;
negating values of the second long pass wavelength band data set;
combining the first long pass wavelength band data set and the negated second long pass wavelength band data set to generate a first pass band that selects image data from the sample with wavelengths between the first and second cut-off wavelengths;
processing the selected image data in the first pass band to identify marked objects in the sample;
selecting, during operation of the imaging system, a different one of the first or second of the long pass wavelength band data sets having a different first or second cut-off wavelength and generating therefrom a second pass band different from the first pass band;
selecting image data from the sample with wavelengths in the second pass band; and
processing the selected image data in the second pass band to identify marked objects in the sample.

20. A method for imaging a sample, comprising:
illuminating a sample with one or more wavelengths of light;
detecting with an image sensor light from the illuminated sample;
filtering with a linear variable short pass filter light reflected from the sample to pass to the image sensor multiple different wavelength bands having different cut-off wavelengths, where wavelengths of light on one side of the cut-off wavelength are blocked and wavelengths of light on the other side of the cut-off wavelength are passed as multiple different short pass wavelength bands for detection by the image sensor;
the image sensor detecting light for each of the multiple different short pass wavelength bands from the sample;
converting the detected light for the multiple different short pass wavelength bands for the sample into corresponding different short pass wavelength band data sets for the sample;
dynamically selecting during operation of the imaging system a first one of the short pass wavelength band data sets having a first cut-off wavelength and a second different one of the short pass wavelength band data sets having a second different cut-off wavelength;
negating values of the second short pass wavelength band data set;
combining the first short pass wavelength band data set and the negated second short pass wavelength band data set to generate a first pass band that selects image data from the sample with wavelengths between the first and second cut-off wavelengths;
processing the selected image data in the first pass band to identify marked objects in the sample;
selecting, during operation of the imaging system, a different one of the first or second of the short pass wavelength band data sets having a different first or second cut-off wavelength and generating therefrom a second pass band different from the first pass band;
selecting image data from the sample with wavelengths in the second pass band; and
processing the selected image data in the second pass band to identify marked objects in the sample.

* * * * *